US008084573B2

(12) United States Patent
Jagota et al.

(10) Patent No.: US 8,084,573 B2
(45) Date of Patent: Dec. 27, 2011

(54) CARBON NANOTUBE BINDING PEPTIDES

(75) Inventors: Anand Jagota, Bethlehem, PA (US); Steven Raymond Lustig, Landenberg, PA (US); Siqun Wang, Wilmington, DE (US); Hong Wang, Kennett Square, PA (US)

(73) Assignee: E.I. Du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/895,933

(22) Filed: Oct. 1, 2010

(65) Prior Publication Data

US 2011/0020902 A1 Jan. 27, 2011

Related U.S. Application Data

(62) Division of application No. 11/352,582, filed on Feb. 13, 2006, now Pat. No. 7,829,504.

(51) Int. Cl.
*A61K 38/04* (2006.01)
*C40B 40/02* (2006.01)
(52) U.S. Cl. .................. 530/327; 506/14; 977/705
(58) Field of Classification Search .................. 530/327; 506/14; 977/705
See application file for complete search history.

(56) References Cited

U.S. PATENT DOCUMENTS

| | | | |
|---|---|---|---|
| 5,223,409 A | 6/1993 | Ladner et al. |
| 5,403,484 A | 4/1995 | Ladner et al. |
| 5,571,698 A | 11/1996 | Ladner et al. |
| 5,652,131 A | 7/1997 | Beavo et al. |
| 5,770,687 A | 6/1998 | Hornik et al. |
| 5,824,470 A | 10/1998 | Baldeschwieler et al. |
| 5,837,500 A | 11/1998 | Ladner et al. |
| 5,866,434 A | 2/1999 | Massey et al. |
| 6,287,765 B1 | 9/2001 | Cubicciotti et al. |
| 6,365,711 B1 | 4/2002 | Whitman et al. |
| 6,376,177 B1 | 4/2002 | Poponin et al. |
| 6,426,134 B1 | 7/2002 | Lavin et al. |
| 6,551,795 B1 | 4/2003 | Rubenfield et al. |
| 6,574,130 B2 | 6/2003 | Segal et al. |
| 6,639,130 B2 | 10/2003 | Jang et al. |
| 6,747,137 B1 | 6/2004 | Weinstock et al. |
| 6,833,447 B1 | 12/2004 | Goldman et al. |
| 6,979,557 B2 | 12/2005 | Isogai et al. |
| 2003/0021966 A1 | 1/2003 | Segal et al. |
| 2003/0022428 A1 | 1/2003 | Segal et al. |
| 2003/0068900 A1 | 4/2003 | Belcher et al. |
| 2003/0166004 A1 | 9/2003 | Gyuris et al. |
| 2007/0117149 A1* | 5/2007 | Jagota et al. .................. 435/7.1 |

FOREIGN PATENT DOCUMENTS

| | | |
|---|---|---|
| EP | 0 503 683 A1 | 9/1992 |
| WO | WO 92/22571 A1 | 12/1992 |
| WO | WO 97/32571 A1 | 9/1997 |
| WO | WO 99/57564 A1 | 11/1999 |
| WO | WO 01/16155 A1 | 3/2001 |
| WO | WO 02/48701 A2 | 6/2002 |
| WO | WO 03/021613 A2 | 7/2002 |
| WO | WO 03/016901 A1 | 2/2003 |
| WO | WO 03/022733 A2 | 3/2003 |
| WO | WO 03/026590 A2 | 4/2003 |
| WO | WO 03/038033 A2 | 5/2003 |

OTHER PUBLICATIONS

J. Liu et al., Fullerene Pipes, Science 280, 1253, 1998.
A. G. Rinzler, Large-scale purification of single-wall carbon nanotubes: process, product, and characterization, Appl. Phys. 67, 29, 1998.
A. C. Dillion et al., A Simple and Complete Purification of Single-Walled Carbon Nanotube Materials, Adv. Mater. 11, 1354, 1999.
Schlitter at al., Single Crystals of Single-Waslled Carbon Nanotubes formed by Self-Assembly, Science 292: 1136, 2001.
Dixit, S., Combinatorial Chemistry—Principle and Practices, J. of Sci. & Ind. Research, 57, 173-183, 1998.
A. Thess et al., Crystalline Ropes of Metallic Carbon Nanotubes, Science 273, 483, 1996.
C. Jornet et al., Large-scale production of single-walled carbon nanotubes by the electric-arc technique, Nature 388, 756, 1997.
P. Nikolaev et al., Gas-phase catalytic growth of single-walled carbon nanotubes from carbon monoxide, Chem. Phys. Lett. 313, 91-97, 1999.
J. Kong et al., Chemical vapor deposition of methane for single-waqlled carbon nanotubes, Chem. Phys. Lett. 292, 567-574, 1998.
J. Kong et al., Synthesis of individual single-walled carbon nanotubes on patterned silicon wafers, Nature 395, 878-879, 1998.
A. Cassell et al., Large Scale CVD Synthesis of Single-Walled Carbon Nanotubes, J. Phys. Chem. 103, 6484-6492, 1999.
H. Dai et at, Controlled Chemical Routes to Nanoitube Architectures, Physics, and Devices, J. Phys. Chem. 103, 11246-11255, 1999.
Yan Li, et at, Preparation of Monodispersed Fe-Mo Nanoparticles as the Catalyst for CVD Synthesis of Carbon Nanotubes, Chem. Mater.: 13(3), 1008-1014, 2000.
N. Franklin and H. Dai, An Enhanced CVD Approach to Extensive Nanotube Networks with Directionality, Adv. Mater. 12, 890, 2000.
A. Cassell et al., Directed Growth of Free-Standing Single-Walled Carbon Nanotubes, J. Am. Chem. Soc. 121, 7975-7976, 1999.
Wang et al., Peptides with selective affinity for carbon nanotubes, Nature Materials, vol. 2, Mar. 2003.
Hartgerink et al., Peptide Nanotubes and Beyond, Chem. Eur. J., 1998, vol. 4, No. 8, pp. 1367-1372.
Jason J. Davis et. al., The Immobilisation of Proteins in Carbon Nanotubes,.Inorganica Chimica Acta, 1999, pp. 261-266, vol. 272.
Sandra R. Whaley et. al., Selection of Peptides With Semiconductor Binding Specificity for Directed Nanocrystal Assembly, Nature, 2000, pp. 665-668, vol. 405.
Robert J. Chen et. al., Noncovalent Sidewall Functionalization of Single-Walled Carbon Nanotubes for Protein Immobilization, J. Am. Chem. Soc., 2001, pp. 3838-3839, vol. 123.
Siqun Wang et. al., Peptides With Selective Affinity for Carbon Nanotubes, Nature Materials, 2003, pp. 196-200, vol. 2.
Kriplani, Ushma et al., Selecting peptides for use in nanoscale materials using phase-displayed combinatorial peptide libraries, Current Opinion in Biotechnology, 2005, 470-475, vol. 16, Elsevier Ltd.

* cited by examiner

*Primary Examiner* — Amber D. Steele

(57) ABSTRACT

Peptides have been generated that have binding affinity to carbon nanostructures and particularly carbon nanotubes. Peptides of or the invention are generally about twelve amino acids in length. Methods for generating carbon nanotube binding peptides are also disclosed.

3 Claims, 3 Drawing Sheets

A  B  C (a)

(b)

(c)

(d)

CARBON NANOTUBE BINDING PEPTIDES

This application is a Divisional of granted U.S. patent application Ser. No. 11/352,582 filed Feb. 13, 2006, now granted U.S. Pat. No. 7,829,504, which under 35 U.S.C. §120 claims the benefit of U.S. patent application Ser. No. 10/453, 415—filed on Jun. 3, 2003—now U.S. Pat. No. 7,304,128 granted Dec. 4, 2007.

FIELD OF THE INVENTION

The invention relates to methods, and compositions useful for manipulation, purification and characterization of carbon nanotubes. More specifically, the invention relates to peptides that bind carbon based nanostructures, their synthesis and methods of use.

BACKGROUND OF THE INVENTION

Carbon nanotubes (CNT) have been the subject of intense research since their discovery in 1991. CNT's possess unique properties such as small size and electrical conductivity, which makes them suitable in a wide range of applications, including use as structural materials in molecular electronics, nanoelectronic components, and field emission displays. Carbon nanotubes may be either multi-walled (MWNTs) or single-walled (SWNTs), and have diameters in the nanometer range.
Depending on their atomic structure CNT's may have either metallic or semiconductor properties, and these properties, in combination with their small dimensions makes them particularly attractive for use in fabrication of nano-devices.

One of the drawbacks to the implementation of CNT's in nano-device fabrication processes is the difficulty in obtaining samples of CNT's that have uniform lengths, or chirality. Additionally, no facile method is available for the immobilization and manipulation of CNT's for nano-device fabrication.

Most methods of CNT synthesis produce a product that is a mixture of entangled tubes of "ropes", giving CNT's differing in diameter, chirality, and in the number of walls. Various methods such as acid washing, ultra-sonification, polymer wrapping and use of surfactants have been employed for nanotube separation (J. Liu et al. *Science* 280, 1253 (1998); A. G. Rinzler, *Appl. Phys.* 67, 29 (1998); A. C. Dillion et al. *Adv. Mater.* 11, 1354 (1999); (Schlittler et al. *Science* 292:1136 (2001)).). However, there has been no report of a method for the specific disentangling of nanotube ropes or their separation into populations having discrete sizes, chirality or conducting properties.

Because of their ability to specifically recognize substrates, various proteins represent one possible route to solving the CNT separation/purification problem as well as providing a possible means for CNT immobilization. Some attempts have been made to raise antibodies to various carbon based structures. For example, Chen et al. (WO 01/16155 A1) used conjugated fullerenes to raise monoclonal antibodies to $C_{60}$ fullerene as a hapten. However, the population of antibodies raised by immunization of mice with this $C_{60}$ fullerene derivative which was conjugated to bovine thyroglobulin included a sub-population that cross reacted with a $C_{70}$ fullerene. No attempts have been made to date to raise antibodies to carbon based nanotubes.

Since its introduction in 1985 phage display has been widely used to discover a variety of ligands including peptides, proteins and small molecules for drug targets. (Dixit, S., *J. of Sci. & Ind. Research*, 57, 173-183, 1998). The applications have expanded to other areas such as studying protein folding, novel catalytic activities and DNA-binding proteins with novel specificities. Whaley et al (*Nature*, 405:665 (2000)) has used phage display technique to identify peptide sequences that can bind specifically to different crystallographic forms of inorganic semiconductor substrates. Although the method of generating large, diverse peptide libraries with phage display has been known for some time, it has not been applied to the problem of finding peptides that may be useful in the binding and manipulation of CNT's.

The problem to be solved, therefore, is to provide materials that have binding specificity to CNT's and other carbon based nanostructures so that they may be used in separation and immobilization of these structures for the fabrication of nano-devices. Applicants have solved the stated problem by providing a series of carbon nanotube binding peptides with high affinity and specificity for CNT's.

SUMMARY OF THE INVENTION

In one aspect the invention provides a process for generating a carbon nanostructure binding peptide comprising a composition comprising a solid substrate coated with a peptide having an amino acid sequence selected from the group consisting of SEQ ID No: 115-121, 123, 125 and 126.

Provided herein are also compositions comprising a solid substrate coated with a carbon nanotube binding peptide, as well as compositions comprising a solid substrate coated with a carbon nanotube binding peptide having at least one carbon nanotube bound thereto.

BRIEF DESCRIPTION OF THE FIGURES AND SEQUENCE LISTINGS

Figure 1:
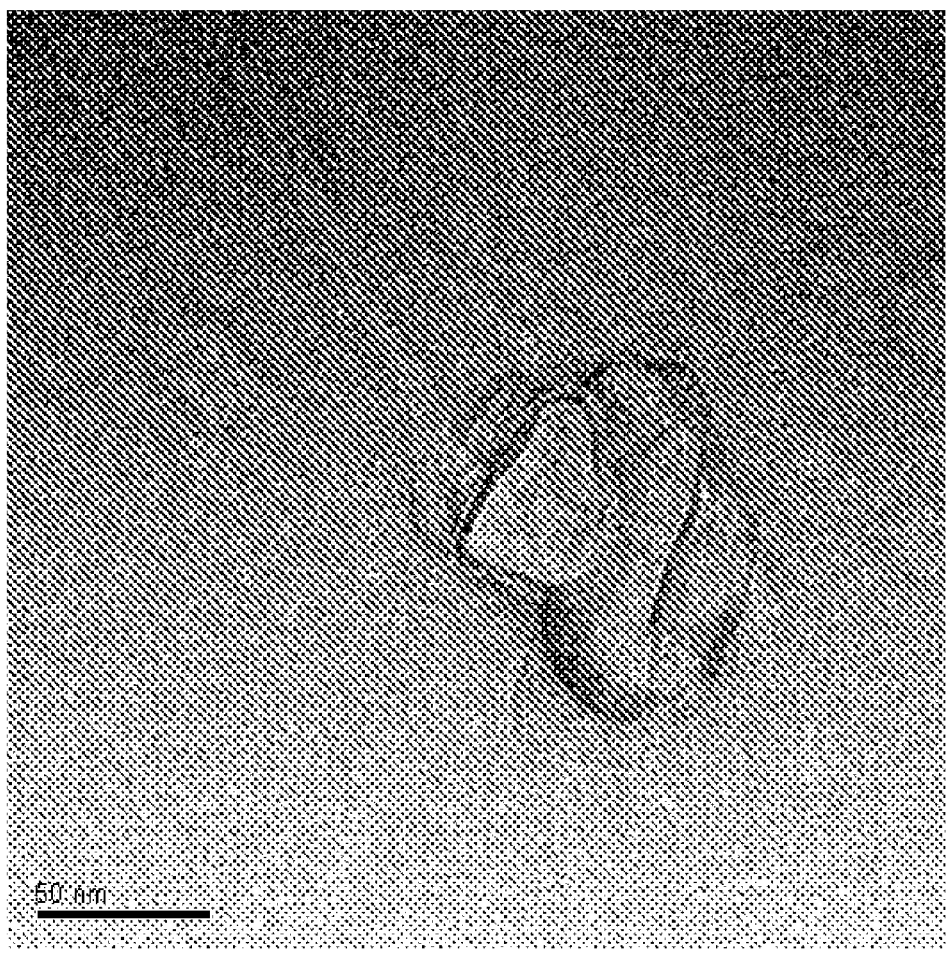
FIG. 1 is a TEM image of phages with carbon nanotube binding peptides on surface of carbon nanotubes.

The following sequences conform with 37 C.F.R. 1.821-1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID Nos:1-24 and 35-39 are carbon nanotube binding peptides of the invention.

SEQ ID NOs:25, and 32 are derivatized carbon nanotube binding peptides having a polyglycine tail.

SEQ ID Nos:26 and 27 are mutant carbon nanotube binding peptides having a serine substituted in place of a tryptophan at position 6.

SEQ ID NO:28 is a control peptide that have little or no binding affinity for carbon nanostructures.

SEQ ID NO:29 is a charged portion of a carbon nanotube binding peptide.

SEQ ID NO:30 is a polar portion of a carbon nanotube binding peptide.

SEQ ID NO:31 is a hydrophobic portion of a carbon nanotube binding peptide.

SEQ ID NO:33 is a primer used for sequencing M13 phage.

SEQ ID NO:34 is a non-CNT binding peptide.

SEQ ID NOs:40-85 are peptides raised against and binding to single walled nanotoubes.

SEQ ID NOs:86-147 and 177 are peptides raised against and binding to multiwalled carbon nanotubes.

SEQ ID NOs:148-176 are peptides raised against and binding to granphite cleaned carbon nanotubes.

DETAILED DESCRIPTION OF THE INVENTION

The present invention provides various carbon nanotube binding peptides generated by the process of peptide phage display. The peptides are useful for the manipulation of carbon based nanostructures in the fabrication of nano-devices as well as in the separation and purification of nanotubes from mixed CNT populations.

The peptides of the invention are particularly useful as ligands for the assembly of carbon nanotubes and related molecules into conducting nano devices for use in electronic applications such as field-emission transistors, artificial actuators, molecular-filtration membranes, energy-absorbing materials, molecular transistors, and other optoelectronic devices as well as in gas storage, single-electron devices, and chemical and biological sensors.

In this disclosure, a number of terms and abbreviations are used. The following definitions are provided.

"CNBP" means Carbon nanotube binding peptide
"HRTEM" means high-resolution transmission electron microscopy
"MWNT" means Multi-walled nanotube
"SWNT" means Single walled nanotube
"PEG" means polyethylene glycol
"pfu" means plaque forming units
"TEM" means transmission electron microscopy
"CNT" means carbon nanotube The term "peptide" refers to two or more amino acids joined to each other by peptide bonds or modified peptide bonds. Peptides include those modified either by natural processes, such as processing and other post-translational modifications, but also chemical modification techniques. The modifications can occur anywhere in a peptide, including the peptide backbone, the amino acid side chain, and the amino or carboxyl terminal. Examples of modifications include but are not limited to amidation, acylation, acetylation, cross linking, cyclization, glycosylation, hydroxylation, phosphorylation, racemization, and covalent attachment of various moieties such as nucleotide or nucleotide derivative, lipid or lipid derivatives (see, for instance, Proteins-Structure and Molecular Properties, $2^{nd}$ Ed Creighton, W. H. Freeman and Company, New York (1993) and Post-translation covalent Modification of Proteins, B. C. Johnson, Ed., Academic Press, New York (1983)).

As used herein, the term "peptide" and "polypeptide" will be used interchangeably.

The term "nanotube" refers to a hollow article having a narrow dimension (diameter) of about 1-200 nm and a long dimension (length), where the ratio of the long dimension to the narrow dimension, i.e., the aspect ratio, is at least 5. In general, the aspect ratio is between 10 and 2000.

By "carbon-based nanotubes" or "carbon nanotube" herein is meant hollow structures composed primarily of carbon atoms. The carbon nanotube can be doped with other elements, e.g., metals.

The term "carbon nanotube product" refers to cylindrical structures made of rolled-up graphene sheet, either single-wall carbon nanotubes or multi-wall carbon nanotubes.

The term "carbon nanotube rope" means a population of non-aligned nanotubes.

The term "carbon nanostructure binding peptide" refers to peptides that were selected to bind with a carbon nanostructures. Where peptides are generated with specific affinity to carbon nanotubes, these peptides will be referred to as carbon nanotube binding peptides or CNBP's.

The term "stringency" as it is applied to the selection of CNBP's means the concentration of eluting agent (usually detergent) used to elute peptides from CNT's.

The term "peptide-nanotube complex" means structure comprising a peptide bound to a nanotube via a binding site on the peptide.

The term "nano-structure" means tubes, rods, cylinders, bundles, wafers, disks, sheets, plates, planes, cones, slivers, granules, ellipsoids, wedges, polymeric fibers, natural fibers, and other such objects which have at least one characteristic dimension less than about 100 nm.

The term "solid substrate" means a material to which a carbon nanotube or binding peptide may be affixed either by direct chemical means or via an intermediate material such as a coating.

The term "identity" refers to a relationship between two or more polynucleotide sequences or two or more polypeptide sequences, as determined by comparing the sequences. "Identity" and "similarity" can be readily calculated by known methods including but not limited to those described in (Sequence Analysis in Molecular Biology, Von Heinje, G., Academic Press, 1987, Sequence analysis Primer, Gribskov, M. and Devereux, J., eds., M Stockton Press, New York, 1991, and Computer Analysis of Sequence Data, Part 1, Griffin, A. M., and Griffin, H. G., eds, Humana Press, New Jersey, 1994.

The term "amino acid" will refer to the basic chemical structural unit of a protein or polypeptide. The following abbreviations will be used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamine acid | Glu | E |
| Glutamine or glutamic acid | Glx | Z |
| Glycine | Gly | G |
| Histidine | His | H |
| Leucine | Leu | L |
| Lysine | Lys | K |
| Methionine | Met | M |
| Phenylalanine | Phe | F |
| Proline | Pro | P |

-continued

| Amino Acid | Three-Letter Abbreviation | One-Letter Abbreviation |
|---|---|---|
| Serine | Ser | S |
| Threonine | Thr | T |
| Tryptophan | Trp | W |
| Tyrosine | Tyr | Y |
| Valine | Val | V |

The term "variant(s)" refers to a polynucleotide, or polypeptide, that differs from a reference polynucleotide, or polypeptide, respectively, but retains essential properties. Changes in the nucleotide sequence of the variant may or may not alter the amino acid sequence of polypeptide encoded by the reference polynucleotide. Nucleotide changes may result in amino acid substitutions, deletions, additions, fusions, and truncations in the polypeptide encoded by the reference sequence. A typical variant of a polypeptide may differ in amino acid sequence from another reference polypeptide by one or more substitutions, additions, deletions in any combinations. A substituted or inserted amino acid residue may or may not be one encoded by the genetic code. A variant of a polynucleotide or polypeptide may be a naturally occurring such as allelic variant, or may not be known as naturally occurring variant. Non-naturally occurring variants of polynucleotides and polypeptides may be made by direct synthesis, mutagenesis techniques, or by other recombinant methods known in the art.

The term "chemically equivalent amino acid" will refer to an amino acid that may be substituted for another in a given protein without altering the chemical or functional nature of that protein. For example, it is well known in the art that alterations in a gene which result in the production of a chemically equivalent amino acid at a given site, but do not effect the functional properties of the encoded protein are common. For the purposes of the present invention substitutions are defined as exchanges within one of the following five groups:

Hydrophobic
    Small aliphatic, nonpolar or slightly polar residues: Ala, Ser, Thr Pro, Gly;
    Large aliphatic, nonpolar residues: Met, Leu, Ile, Val Cys; and
    Large aromatic residues: Phe, Tyr, Trp;
Hydrophilic:
    Polar, negatively charged residues and their amides: Asp, Asn, Glu, Gln;
    Polar, positively charged residues: H is, Arg, Lys;

Thus, alanine, a hydrophobic amino acid, may be substituted by another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. Additionally, in many cases, alterations of the N-terminal and C-terminal portions of the protein molecule would also not be expected to alter the activity of the protein.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "expression", as used herein, refers to the transcription and stable accumulation of sense (mRNA) or antisense RNA derived from the nucleic acid fragment of the invention. Expression may also refer to translation of mRNA into a polypeptide.

The term "transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The term "host cell" refers to cell which has been transformed or transfected, or is capable of transformation or transfection by an exogenous polynucleotide sequence.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "phage" or "bacteriophage" refers to a virus that infects bacteria. Altered forms may be used for the purpose of the present invention. The preferred bacteriophages are derived from two "wild" phages, called M13 and lambda. Lambda phages are used to clone segments of DNA in the range of around 10-20 kb. They are lytic phages, i.e., they replicate by lysing their host cell and releasing more phages. The M13 system can grow inside a bacterium, so that it does not destroy the cell it infects but causes it to make new phages continuously. It is a single-stranded DNA phage.

The term "phage display" refers to the display of functional foreign peptides or small proteins on the surface of bacteriophage or phagemid particles. Genetically engineered phage could be used to present peptides as segments of their native surface proteins. Peptide libraries may be produced by populations of phage with different gene sequences.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

The present invention provides peptides that bind carbon nanostructures as well as methods for generating the same and uses thereof.

Carbon Nanostructures

The invention relates to the generation of peptides with binding affinities for carbon nanostructures, and particularly nanotubes. Carbon nano-structures of the present invention are those structures comprised at primarily of carbon which take the form of tubes, rods, cylinders, bundles, wafers, disks, sheets, plates, planes, cones, slivers, granules, ellipsoids, wedges, polymeric fibers, natural fibers, and other such objects which have at least one characteristic dimension less than about 100 nm. Preferred carbon nanstrucutres of the invention are nanotubes.

Nanotubes of the invention are generally about 1-200 nm in diameter where the ratio of the length dimension to the narrow dimension, i.e., the aspect ratio, is at least 5. In general, the aspect ratio is between 10 and 2000. Carbon nanotubes are comprised primarily of carbon atoms, however may be doped with other elements, e.g., metals. The carbon-based nanotubes of the invention can be either multi-walled nanotubes (MWNTs) or single-walled nanotubes (SWNTs). A MWNT, for example, includes several concentric nanotubes each having a different diameter. Thus, the smallest diameter tube is encapsulated by a larger diameter tube, which in turn, is encapsulated by another larger diameter nanotube. A SWNT, on the other hand, includes only one nanotube.

Carbon nanotubes (CNT) may be produced by a variety of methods, and are additionally commercially available. Methods of CNT synthesis include laser vaporization of graphite (A. Thess et al. *Science* 273, 483 (1996)), arc discharge (C. Journet et al., *Nature* 388, 756 (1997)) and HiPCo (high pressure carbon monoxide) process (P. Nikolaev et al. *Chem. Phys. Lett.* 313, 91-97 (1999)). Chemical vapor deposition (CVD) can also be used in producing carbon nanotubes (J. Kong et al. *Chem. Phys. Lett.* 292, 567-574 (1998); J. Kong et al. *Nature* 395, 878-879 (1998); A. Cassell et al. *J. Phys. Chem.* 103, 6484-6492 (1999); H. Dai et al. *J. Phys. Chem.* 103, 11246-11255 (1999)).

Additionally CNT's may be grown via catalytic processes both in solution and on solid substrates (Yan Li, et al., *Chem. Mater.;* 2001; 13(3); 1008-1014); (N. Franklin and H. Dai *Adv. Mater.* 12, 890 (2000); A. Cassell et al. *J. Am. Chem. Soc.* 121, 7975-7976 (1999)).

Peptide Generation

Peptides of the invention are generated randomly and then selected against a population of carbon nanostructures for binding affinity to CNT's. The generation of random libraries of libraries of peptides is well known and may be accomplished by a variety of techniques including, bacterial display (Kemp, D. J.; *Proc. Natl. Acad. Sci. USA* 78(7): 4520-4524, 1981, and Helfman, D. M., et al., *Proc. Natl. Acad. Sci. USA* 80(1): 31-35, 1983) yeast display (Chien C T, et al., *Proc Natl Acad Sci USA* 1991 Nov. 1; 88(21): 9578-82) combinatorial solid phase peptide synthesis (U.S. Pat. No. 5,449,754, U.S. Pat. No. 5,480,971, U.S. Pat. No. 5,585,275, U.S. Pat. No. 5,639,603) and phage display technology (U.S. Pat. No. 5,223,409; U.S. Pat. No. 5,403,484; U.S. Pat. No. 5,571,698; U.S. Pat. No. 5,837,500). Techniques to generate such biological peptide libraries are described in Dani, M., *J. of Receptor & Signal Transduction Res.*, 21(4), 447-468 (2001).

A preferred method to randomly generate peptides is by phage display. Phage display is an in vitro selection technique in which a peptide or protein is genetically fused to a coat protein of a bacteriophage, resulting in display of fused protein on the exterior of phage viron, while the DNA encoding the fusion residues within the virion. This physical linkage between the displayed protein and the DNA encoding it allows screening of vast numbers of variants of proteins, each linked to a corresponding DNA sequence, by a simple in vitro selection procedure called "biopanning." In its simplest form, biopanning is carried out by incubating the pool of phage-displayed variants with a target of interest that has been immobilized on a plate or bead, washing away unbound phage, and eluting specifically bound phage by disrupting the binding interactions between the phage and target. The eluted phage is then amplified in vivo and the process repeated, resulting in stepwise enrichment of the phage pool in favor of the tightest binding sequences. After 3 or more rounds of selection/amplification, individual clones are characterized by DNA sequencing.

Thus it is an object of the invention to provide a process for generating a carbon nanostructure binding peptide comprising:
 a) providing a library of phages expressing peptides in solution;
 b) providing a population of carbon nanostructures;

c) contacting the phage of (a) with the nanostructures of (b) for a time sufficient to permit binding of the phage to the nanostructures and forming a phage-nanostructure complex;
d) removing unbound phage;
e) contacting the phage-nanostructure complex of (c) with a suitable bacterial host whereby the bacteria are infected by the phage;
f) growing the infected bacteria of step (e) for a time sufficient to permit replication of the phage and the expressed peptide; and
g) isolating the replicated phage and expressed peptide of step (f) wherein the peptide binds carbon nanostructures.

Peptide Selection

After a suitable library of peptides has been generated they are then contacted with an appropriate population of carbon nanostructures or nanotubes. The nanotubes are presented to the library of peptides typically while suspended in solution, although it will be appreciated that CNT or peptides could also be immobilized on a solid substrate to facilitate binding. In such an embodiment suitable solid substrates will include but are not limited to silicon wafers, synthetic polymer substrates, such as polystyrene, polypropylene, polyglycidyl-methacrylate, substituted polystyrene (e.g., aminated or carboxylated polystyrene; polyacrylamides; polyamides; polyvinylchlorides, etc.); glass, agarose, nitrocellulose, and nylon.

A preferred solution is a buffered aqueous saline solution containing a surfactant. A suitable solution is Tris-buffered saline with 0.1% Tween 20. The solution can additionally be agitated by any means in order to increase binding of the peptides to the nanotubes.

Upon contact a number of the randomly generated peptides will bind to the CNT's to form a peptide-nanotube complex. Unbound peptide and CNT may be removed by washing (if immobilized) or by any other means such as centrifugation, or filtering, etc. After all unbound material is removed, peptides, having varying degrees of binding affinities for CNT's may be fractionated by selected washings in buffers having varying strengths of surfactants. The higher the concentration of surfactant in the wash buffer, the higher the stringency of selection. Increasing the stringency used will increase the required strength of the bond between the peptide and nanotube in the peptide-nanotube complex.

A number of materials may be used to vary the stringency of the buffer solution in peptide selection including but not limited to acidic pH 1.5-3; basic pH 10-12.5; high salt concentrations such as MgCl2 3-5 M, LiCl 5-10 M; water; ethylene glycol 25-50%; dioxane 5-20%; thiocyanate 1-5 M; guanidine 2-5 M; urea 2-8 M; various concentrations of different surfactants such as SDS (sodium dodecyl sulfate), DOC (sodium deoxycholate), Nonidet P-40, Triton X-100, Tween 20® wherein Tween 20® is preferred. The materials can be prepared in buffer solutions including but not limited to Tris-HCl, Tris-borate, Tris-acidic acid, triethylamine, phosphate buffer, glycine-HCl wherein 0.25M glycine-HCl solution is preferred.

It will be appreciated that peptides having greater and greater binding affinities for the CNT substrate may be eluted by repeating the selection process using buffers with increasing stringencies.

The eluted peptides can be identified, sequenced, and produced by any means known in the art.

Carbon Nanotube Binding Peptides

Peptides of the invention selected by the above process have been identified. A large number of peptides having particularly high binding affinities to carbon nanotubes were isolated having the amino acid sequences as set forth in SEQ ID NOs:1-24 and 35-177

It will be appreciated by the skilled artisan that the invention is not limited to these specific sequences but will include amino acid sequences comprising chemically equivalent amino acid substitutions that do not interfere with the ability of the peptide to bind CNT's. So for example, the chemically equivalent substitutions for each of the amino acids in SEQ ID NO:14 are detailed in the following table:

| SEQ ID NO: 14 | His Trp Ser Ala Trp Trp Ile Arg Ser Asn Gln Ser | |
|---|---|---|
| Equivalent Amino Acids | Lys Phe Pro Ser Phe Phe | Lys Pro Asp Asp Pro |
| | Arg Tyr Ala Pro Tyr Tyr | His Ala Glu Asn Ala |
| | Thr Thr | Thr Gln Glu Thr |
| | Gly Gly | Gly  Gly |

Alignment and analysis of the selected peptides of the invention suggests that the carbon nanostructure or nanotube binding properties are related to the secondary characteristics of the peptide. For example a simple pendant model was developed for the peptides of the instant invention, which accounts for hydrophilicity or hydrophobicity. It demonstrates that all of the consensus sequences are essentially symmetric surfactants-hydrophilic on the ends and hydrophobic in the middle. The model describes the degree of hydrophilicity or hydrophobicity of an amino acid pendant group by classifying all pendant groups as either hydrophilic ($h=-1$) or hydrophobic ($h=1$). Side chains which are either basic, acidic or uncharged polar are be hydrophilic while side chains that are nonpolar are hydrophobic. Several of the peptides selected by the methods of the invention are modeled below:

```
                                           (SEQ ID NO: 1)
         H  A  H  S  Q  W  W  H  L  P  Y  R
        -1  1 -1 -1 -1  1  1 -1  1  1 -1 -1

(SEQ ID NO: 13)
         H  W  K  H  P  W  G  A  W  D  T  L
        -1  1 -1 -1  1  1  1  1  1 -1 -1  1

(SEQ ID NO: 14)
         H  W  S  A  W  W  I  R  S  N  Q  S
        -1  1 -1  1  1  1  1 -1 -1 -1 -1 -1

(SEQ ID NO: 8)
         H  N  W  Y  H  W  W  M  P  H  N  T
        -1 -1  1 -1 -1  1  1  1  1 -1 -1 -1
```

These peptides were selected over a broad range of detergent concentrations (0.6%-3%) and yet show the same pattern of hydrophilicity and hydrophobicity. With a few exceptions, the $h=-1$ are predominantly on the ends and $h=1$ are concentrated in the middle.

It is thus an object of the invention to provide a carbon nanotube binding peptides having the general structure:

N-M-C

Wherein:
N is the N-terminal portion of the peptide having about 4 amino acids, 75% of which are hydrophilic;
M is the median portion of the peptide having about 4 amino acids, 75% of which are hydrophobic; and
C is the C-terminal portion of the peptide having about 4 amino acids 75% of which are hydrophilic.

Peptide Production by Recombinant Methods

Once a peptide having suitable binding properties is identified it may be produced recombinantly in large quantities. Genes encoding nanotube binding peptides may be produced in heterologous host cells, particularly in the cells of microbial hosts.

Preferred heterologous host cells for expression of nanotube binding peptides are microbial hosts that can be found broadly within the fungal or bacterial families and which grow over a wide range of temperature, pH values, and solvent tolerances. Because of transcription, translation and the protein biosynthetic apparatus is the same irrespective of the cellular feedstock, functional genes are expressed irrespective of carbon feedstock used to generate cellular biomass. Examples of host strains include but are not limited to fungal or yeast species such as *Aspergillus, Trichoderma, Saccharomyces, Pichia, Candida, Hansenula*, or bacterial species such as *Salmonella, Bacillus, Acinetobacter, Rhodococcus, Streptomyces, Escherichia, Pseudomonas, Methylomonas, Methylobacter, Alcaligenes, Synechocystis, Anabaena, Thiobacillus, Methanobacterium* and *Klebsiella*.

A variety of expression systems can be used to produce the peptides of the present invention. Such vectors include but are not limited to chromosomal, episomal and virus-derived vectors, e.g., vectors derived from bacterial plasmids, from bacteriophage, from transposons, from insertion elements, from yeast episoms, from viruses such as baculaviruses, retroviruses and vectors derived from combinations thereof such as those derived from plasmid and bacteriophage genetic elements, such as cosmids and phagemids. The expression system constructs may contain regulatory regions that regulate as well as engender expression. In general, any system or vector suitable to maintain, propagate or express polynucleotide or polypeptide in a host cell may be used for expression in this regard. Microbial expression systems and expression vectors contain regulatory sequences that direct high level expression of foreign proteins relative to the growth of the host cell. Regulatory sequences are well known to those skilled in the art and examples include but are not limited to those which cause the expression of a gene to be turned on or off in response to a chemical or physical stimulus, including the presence of a regulatory elements may also be present in the vector, for example, enhancer sequences. Any of these could be used to construct chimeric genes for production of the any of the nanotube binding peptides. These chimeric genes could then be introduced into appropriate microorganisms via transformation to provide high level expression of the peptides.

Vectors or cassettes useful for the transformation of suitable host cells are well known in the art. Typically the vector or cassette contains sequences directing transcription and translation of the relevant gene, one or more selectable markers, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host. Selectable marker genes provide a phenotypic trait for selection of the transformed host cells such as tetracyclin or ampicillin resistance in *E. coli*.

The gene can be placed under the control of a promoter, ribosome binding site (for bacterial expression) and, optionally, an operator or control element, so that Initiation control regions or promoters, which are useful to drive expression of the instant ORF's in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, $IP_L$, $IP_R$, T7, tac, and trc (useful for expression in *Escherichia coli*) as well as the amy, apr, npr promoters and various phage promoters useful for expression in *Bacillus*.

Termination control regions may also be derived from various genes native to the preferred hosts. Optionally, a termination site may be unnecessary, however, it is most preferred if included.

The vector containing the appropriate DNA sequence as here in above described, as well as an appropriate promoter or control sequence, may be employed to transform an appropriate host to permit the host to express the peptide of the present invention. Cell-free translation systems can also be employed to produce such peptides using RNAs derived from the DNA constructs of the present invention.

Optionally it may be desired to produce the instant gene product as a secretion product of the transformed host. Secretion of desired proteins into the growth media has the advantages of simplified and less costly purification procedures. It is well known in the art that secretion signal sequences are often useful in facilitating the active transport of expressible proteins across cell membranes. The creation of a transformed host capable of secretion may be accomplished by the incorporation of a DNA sequence that codes for a secretion signal which is functional in the host production host. Methods for choosing appropriate signal sequences are well known in the art (see for example EP 546049; WO 9324631). The secretion signal DNA or facilitator may be located between the expression-controlling DNA and the instant gene or gene fragment, and in the same reading frame with the latter.

Nano-Device Fabrication

The carbon nanotube binding peptides (CNBP) of the instant invention could be one element in an entity with bi-, tri- (or higher) binding functionality. A CNBP can be depicted graphically as shown below,

where the "C" is suggestive of a carbon nanotube and a binding functionality depicted by "⊂". However, despite its being drawn at one end, it should be interpreted as a collective, not localized, property of the peptide sequence. The overall entity would be constructed by "fusion" of the CNBP with another body, depicted by "B", with a binding functionality depicted by ">", and the combination is represented graphically below

This is meant to represent a minimal example; the fusion could create higher order (enumerative) functionality. Examples of B include but are not limited to a DNA binding protein, a metallic electrode, for example Au bound directly to an amino-acid residue like cysteine, or a hard (e.g., Si or $SiO_2$) substrate for immobilization of the CNBP.

Directed self-assembly of carbon nanotubes into useful structures could be achieved by combining the binding of CNBP with a pre-patterned substrate. For example, if the binding functionality "B" was a series of cysteine residues, the sequence of (a) preparation of a dilute suspension of carbon nanotubes, (b) functionalization of selected types by CNBP, and (c) washing over a substrate with patterned Au electrodes would result in the attachment of carbon nanotubes to metal electrodes via the peptide, within distances of relevance to nano-electronic devices. Because of the diversity of the bio-chemical toolkit in combining elements to obtain higher order functionality, many other such methods can be conceived, once the fundamental binding motifs have been identified.

A major obstacle to the use of carbon nanotubes in a variety of applications is the fact that all manufacturing processes produce a mixture of entangled tubes. Individual tubes in the product differ in diameter, chirality, and number of walls. Moreover, long tubes show a strong tendency to aggregate into "ropes". These ropes are formed due to the large surface areas of nanotubes and can contain tens to hundreds of nanotubes in one rope. Furthermore, the structure of individual tubes varies widely from armchair, zig-zag or other chiral forms which coexist in the material and their electrical properties also vary dramatically accordingly (metallic or semi-conductive). Therefore, a need exists for the isolation of a single form (such as armchair, zig-zag or a chiral form) of carbon nanotubes.

Existing methods for separating such product, for example acid washing, ultra-sonification, and use of surfactants, is non-specific with respect to the type of nanotube. Because peptide binding is usually highly specific, a major utility of a CNBP is to effect specific separation. One possible method would use dilute suspensions of carbon nanotubes separated by having them flow over substrates patterned with different types of binding CNBP's. One would choose to order the patterning based on strength and specificity of binding, i.e., strongly selective binding peptides would be positioned to act on the mixture in advance of less specific ones. Many other ways to achieve separation can be conceived. If "B" binds to a magnetic particle, the joint entity could be used in one stage of a continuous flow to bind to carbon nanotubes, while in another stage the bound nanotubes could be separated magnetically.

Thus it is an object of the invention to provide a method of dispersing a population of carbon nanotube ropes comprising:

a) providing a population of carbon nanotubes in solution in rope formation; and
b) contacting the population of carbon nanotubes of step (a) with a carbon nanotube binding peptide having the general structure:

N-M-C wherein:
N is the N-terminal portion of the peptide having about 4 amino acids, 75% of which are hydrophilic;
M is the median portion of the peptide having about 4 amino acids, 75% of which are hydrophobic; and
C is the C-terminal portion of the peptide having about 4 amino acids 75% of which are hydrophilic;
whereby the carbon nanotube ropes are dispersed.

One of skill in the art will appreciate that it will be useful to sort populations of nanotubes to select for various binding properties. It is contemplated that CNT-binding peptides or isolated phage expressing a CNT binding peptide, may be used for this purpose. For example, CNT-binding peptides or phages expressing the same, having an affinity to a specific population of CNT's may be immobilized on a solid substrate and then contacted with a mixed population of CNT's. The desired CNT's will bind to the immobilized peptides or phage and the undesired CNT's may be washed free. Alternatively, solid substrates such as beads or microshperes may be coated with CNT-binding peptides or phage and used to assemble CNT's. Materials suitable as solid supports may be made of synthetic polymers such as polyethylene, polypropylene, poly(4-methylbutene), polystyrene, polymethacrylate, poly (ethylene terephthalate), nylon, poly(vinyl butyrate), or other materials such as glass, ceramics, metals, and the like. These materials be used as films, microtiter plates, wells, beads, slides, particles, pins, pegs, or membranes.

Accordingly the invention a method for assembling carbon nanotubes comprising contacting a solid substrate coated with at least one species of carbon nanotube binding peptide with a population of carbon nanotubes whereby the carbon nanotubes bind to the coated substrate and are assembled.

It will be appreciated by the skilled artisan that patterning of CNT-binding peptides on a particular solid support will be a useful technique in the design and fabrication of nanodevices. In some instances patterning may be achieved by partially and selectively masking portions of the support with materials that repel or have no affinity for CNT's. A variety of materials may be used for this purpose, however non-CNT binding peptides of similar physical characteristics to CNT-binding peptides will be particularly suitable. Non-CNT binding peptides are easily selected and identified in the early rounds of any selection process for CNT-binding peptides. These may be used to mask a solid support to effect the pattering of CNT binding on the support. Several examples provided herein include the peptides set forth in SEQ ID NO:28 and 34.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

Materials and Methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Preparation of Phage Library

The phage library used in the present invention was purchased from New England BioLabs (catalog number E8110S, Ph.D.-12 Phage Display Peptide Library Kit). The kit is based on a combinatorial library of random peptide 12-mers fused to a minor coat protein (pIII) of M13 phage. The displayed peptide 12mer is expressed at the N-terminus of pIII, i.e. after the signal peptide is cleaved the first residue of the coat protein is the fist residue of the displayed peptide. The library contains $2.7 \times 10^9$ (100 µl) variants in the displayed epitope. A volume of 10 µl contains about 55 copies of each peptide sequence. To avoid introduce bias into the library, each initial round of experiments were carried out using the original library provided by the manufacture.

Sequencing of Phages

Random M13 phage plaques were picked and single plaque lysates were prepared following manufacture's instruction (New England Labs, Beverly, Mass.). The single stranded phage genome DNA was purified with Qiagene kit (QIAprep Spin M13 kit, Cat. No. 27704). The single stranded DNA were sequenced with −96 gIII sequencing primer (5'-CCCTCATAGTTAGCGTAACG-3'). SEQ ID NO:33 The displayed peptide is located immediately after the signal peptide of gene III.

Multi-Sequence Analysis

Sequences from the phage display experiment were analyzed using software DNA Star (version 5.02) or ClustalW according to software instructions. The alignment provides similarities among the selected sequences and predict important functions of certain amino acid residues.

Example 1

Preparation of Carbon Nanotubes

Carbon nanotubes designated CNT-7 were obtained from Yet-Ming Chiang, Department of Materials Science, MIT, Cambridge, Mass. The nanotubes were prepared by heating SiC (silicon carbide) at 1700° C. under vacuum. Silicon "evaporated" from the sample and left behind the carbon, which formed folded structures of carbon including nanotubes.

Single-walled carbon nanotubes were purchased from CNI (Carbon Nanotechnology Incorporated, Houston, Tex.). These nanotubes were produced by a laser oven technique or a HiPCO (high-pressure carbon monoxide) process (P. Nikolaev et al. Chem. Phys. Lett. 313, 91-97 (1999)).

The CNT-7 sample contained various carbon structures including multi-wall and single-wall carbon nanotubes whereas CNI samples were mostly single wall carbon nanotubes.

Example 2

Selection of Carbon Nanotube Binding Peptides

CNT-7 and CNI carbon nanotubes were suspended in Tris-Buffered-Saline with 0.1% Tween 20 (TBS-T) at a concentration of 1 mg/ml. The carbon nanotube solution was then sonicated by a Branson Sonifier model 450 (Branson Sonic Power Co., Danbury, Conn.) with power output setting between 4 and 5, duty cycle 70-80% for three times. Ten microliters of M13 phage library (containing about $10^{11}$ phage) were added to 1 ml of carbon nanotubes. The mixture was incubated at room temperature with mild agitation for 60 minutes. Unbound phages were separated from the nanotube sample by high speed spin at 14,000 rpm (16,110×g) in an Eppendorf 5415C centrifuge (Brinkmann Instruments Inc., Westbury, N.Y.) for 10 minutes. Subsequently the phage/nanotube complex was washed 10 times each with 1 ml TBS-T in which concentration of Tween-20 increases according to the cycles of selection, as shown in the data below. For example, in one experiment the Tween 20 concentration was increased from 0.2% in round one, to 0.3% in round two, to 0.4% in round 4, to 0.5% in round 5, to 0.6% in round 6, to 0.7% in round 7, to 1% in round 8, to 2% in round 9, 3% in round 10, 6% in round 11 and 10% in round 12. After the last (tenth) washing step, the bound phages were eluted off by incubating with 0.5 ml of 0.25 M glycine-HCl, pH 3.0 for 10-15 minutes at room temperature. The phages and nanotubes were separated by centrifuging at 14,000 rpm (16,110× g) for 10 minutes, with the cleared supernatant containing the eluted phages. The presence and concentration of phages in the supernatant were determined by phage titering. Once the sample confirmed the presence of phages, they were used to inoculate E. coli for phage amplification, and the amplified phage sample was used as the "pool" for next round. In a typical experiment, the entire eluent was added to a 20 ml E. coli culture at early log phase. The culture was further incubated for 4.5 hours at 37° C. to allow phage to propagate. At the end of the incubation, the cultures were spin at 16,000×g for 10 minutes at 4° C. The phages in the cleared supernatant were precipitated with PEG/NaCl at 4° C. After centrifugation, the phages were resuspended in 200 µl PBS and the concentration was determined by titering. This sample is used subsequently as the stock for the next round experiment. To carry out the next round experiment, $10^{11}$ phages were used as input "pool" and the selection process was repeated as described above with increased stringency for washing, i.e. increased concentration of Tween-20. Useful peptides were obtained by selection at detergent concentrations of 0.5% and higher and the amino acid sequences of these peptides are shown in Table 1.

TABLE 1

M13 peptide sequences forCNT-7

| SEQ ID NO: | Sequence |
| --- | --- |
| 1. | DPHHHWYHMHQH |
| 2. | HAHSQWWHLPYR |
| 3. | HAHSRRGHIQHR |
| 4. | HCHHPWGAWHTL |
| 5. | HCWNQWCSRHQT |
| 6. | HGNWSYWWSKPS |
| 7. | HHWHHWCMPHKT |
| 8. | HNWYHWWMPHNT |
| 9. | HNWYRWCIRHNN |
| 10. | HRWYRWSSRNQT |
| 11. | HSSWWLALAKPT |
| 12. | HWCAWWISSNQS |
| 13. | HWKHPWGAWDTL |
| 14. | HWSAWWIRSNQS |
| 15. | HWSPWHRPWYQP |
| 16. | HYSWYSTWWPPV |

TABLE 1-continued

M13 peptide sequences for CNT-7

| SEQ ID NO: | Sequence |
|---|---|
| 17. | HYWWRWWMPNQT |
| 18. | KCHSRHDHIHHH |
| 19. | KSLSRHDHIHHH |
| 20. | KSRSRHDEIHHH |
| 21. | KYRSRHDHIHHH |
| 22. | QWHSRHDHIHHH |
| 35. | HNWYHWWPHNT |
| 36. | HWYKPYHFQSLT |
| 37. | SVSVGMKPSPRP |
| 38. | EAHPQTLGWQRP |
| 39. | HNAYWHWPPSMT |

Binding of these peptides to CNT's is further confirmed by TEM micrographs as shown in FIG. 1, illustrating a number of the subject peptides bound to a single walled CNT.

Example 3

Structural and Functional Characterization of Nanotube Binding Peptides

The following example illustrates the importance of conserved amino acids to the binding affinity of peptides for carbon nanotubes.

Alignment of the selected peptide sequences suggests strongly that histidine at position 1 and tryptophan at position 6 are important for binding. Further analysis of more than one hundred phage clones, shown below in Table 3, revealed that His and Trp are two dominant amino acids in the composition of peptides selected by the display.

TABLE 3

| Amino Acids | Number count | % by weight | % by frequency | Original library (%) | Change relative to original (%) |
|---|---|---|---|---|---|
| Charged:<br>RKHYCDE<br>(SEQ ID NO: 29) | 391 | 36.03 | 33.59 | | |
| Acidic:<br>DE | 37 | 2.84 | 3.18 | | |
| Basic:<br>KR | 89 | 8.51 | 7.65 | | |
| Polar:<br>NCQSTY<br>(SEQ ID NO: 30) | 305 | 22.51 | 26.20 | | |
| Hydrophobic:<br>AILFW<br>(SEQ ID NO: 31) | 376 | 37.62 | 32.3 | | |
| A | 57 | 2.69 | 4.90 | 6.0 | — |
| C | 6 | 0.41 | 0.52 | 0.5 | 0.52 |
| D | 35 | 2.67 | 3.01 | 2.8 | 3.01 |
| E | 2 | 0.17 | 0.17 | 3.1 | 0.17 |
| F | 5 | 0.49 | 0.43 | 3.3 | 0.43 |
| G | 30 | 1.13 | 2.58 | 2.6 | 2.58 |
| H | 217 | 19.73 | 18.64 | 6.3 | — |
| I | 27 | 2.03 | 2.32 | 3.4 | 2.32 |
| K | 38 | 3.23 | 3.26 | 2.8 | 3.26 |
| L | 55 | 4.13 | 4.73 | 9.3 | 4.73 |

TABLE 3-continued

| Amino Acids | Number count | % by weight | % by frequency | Original library (%) | Change relative to original (%) |
|---|---|---|---|---|---|
| M | 25 | 2.17 | 2.15 | 2.6 | 2.15 |
| N | 66 | 4.99 | 5.67 | 4.6 | 5.67 |
| P | 85 | 5.47 | 7.30 | 12.2 | 7.30 |
| Q | 37 | 3.14 | 3.18 | 5.1 | 3.18 |
| R | 51 | 5.28 | 4.38 | 4.7 | 4.38 |
| S | 97 | 5.60 | 8.33 | 10.0 | 8.33 |
| T | 57 | 3.82 | 4.90 | 11.1 | 4.9 |
| V | 6 | 0.39 | 0.52 | 3.9 | 0.52 |
| W | 226 | 27.90 | 19.42 | 2.2 | — |
| Y | 42 | 4.54 | 3.61 | 3.6 | 3.61 |
| B | 0 | 0 | 0 | | |
| Z | 0 | 0 | 0 | | |
| X | 0 | 0 | 0 | | |
| Ter | 0 | 0 | 0 | | |

1. Data is from analysis of 100 clones
2. Original library data is adapted from manufacturer's manual and is from analysis of 104 clones Site-directed mutagenesis was used to introduce mutations in peptides SEQ ID NO:13 (HWKHPWGAWDTL) and SEQ ID NO:14 (HWSAWWIRSNQS) Trp->Ser at position 6, to produce peptides HWKHPSGAWDTL (SEQ ID NO:26) and HWSAWSIRSNQS (SEQ ID NO:27), respectively. The phages carrying these mutations were assayed for their binding activity against CNT-7 at detergent concentration 0.4% as described above. The mutation at Trp6 reduced binding to CNT-7 for both peptides. The data is shown in Table 4 below. The number of plaque forming units is charted for a control peptide (LPPSNASVADYS) SEQ ID NO:28 and peptides SEQ ID NO:13, 14 and mutant peptides SEQ ID NO: 26 and 27. The binding data shown in Table 4 confirms the critical role of Trp in binding to nanotubes.

TABLE 4

| Phage | Pfu |
|---|---|
| SEQ ID NO: 26 | $4.58 \times 10^6$ |
| SEQ ID NO: 27 | $5.4 \times 10^6$ |
| SEQ ID NO: 28 | $6.7 \times 10^6$ |
| SEQ ID NO: 13 | $15.9 \times 10^6$ |
| SEQ ID NO: 14 | $59.2 \times 10^6$ |

Example 4

Effect of Peptide Binding on Populations of Nanotubes

The following example illustrates the ability of carbon nanotube binding peptides to disentangle carbon nanotube "ropes".

Experiments were carried out with synthetic peptides and single-wall carbon nanotubes (CNI/Laser oven) and binding peptides sequence HWKHPWGAWDTLGGG [SEQ ID NO: 25]. This peptide was selected as described in Example 2 and represens the peptide as set forth in SEQ ID NO:13, with the addition of a poly-glycine tail.

Figure 2:
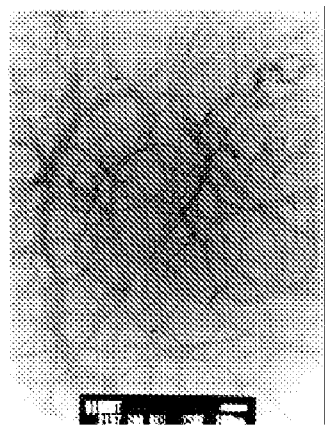
FIG. 2A is an electronmicrograph of untreated nanotubes ropes.
FIG. 2B is an electronmicrograph of single walled nanotubes treated with carbon nanotube binding peptide as set forth in SEQ ID NO:13.
FIG. 2C is an electronmicrograph of single walled nanotubes treated with a control peptide, having little or no binding affinity for CNT's.
Figure 2:
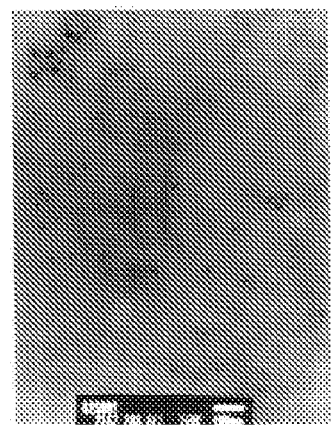
Figure 2:
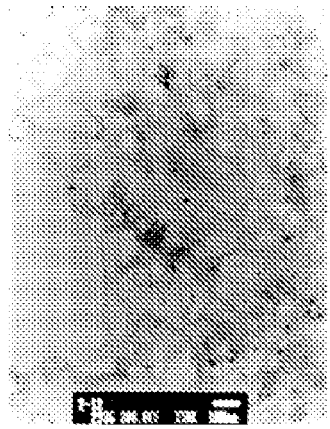

At a concentration of 4 mg/ml peptide of SEQ ID NO:25 was seen to disperse the nanotube ropes as examined by HRTEM whereas the mutant peptide SEQ ID NO:26, containing a polyglycine tail HWKHPSGAWDTLGGG [SEQ ID NO:32] and a control peptide SEQ ID NO:28 did not disperse the nanotube at the same concentration. The results are shown in FIG. 2. Panel A of FIG. 2 is an electron micrograph of nanotubes ropes untreated with any peptide. Panel B of FIG. 2 is an electron micrograph of single walled nanotubes after treatment with the carbon nanotube binding peptide of SEQ ID NO:13 showing dispersement of the nanotubes. Panel C of FIG. 2 is an electron micrograph of single walled nanotubes after treatment with the peptide of SEQ ID NO:28, a control peptide having little or no nanotube binding affinity.

Example 5

Graphite-Cleaned Binding Peptides

In order to find peptides with specific binding to carbon nanotubes, phage display experiments were performed as described in Example 2 on CNT-7 carbon nanotube substrates using a "graphite-cleaned" phage library. The graphite-cleaned phage library was generated by first washing the complete phage library on a pyrolytic graphite substrate. The washed or cleaned library was thus denuded of phage that would bind to Graphite. Highly ordered pyrolytic Graphite (HOPG SPI-2, SPI Supplies, West Chester, Pa.) was attached to a petri dish and a fresh layer of graphite was exposed using a Scotch tape. About $10^{11}$ pfu M13 phage in TBS-0.1% Tween-20® was added to the graphite substrate and allowed to sit for binding for 45-60 minutes at room temperature. Unbound phages were washed away with excess amount of (TBS-T) at defined concentrations of Tween-20®. Bound phages were eluted with Glycine-HCl buffer at pH 2.3. The unbound phage (graphite-cleaned library) were then used to perform phage display experiments on CNT-7 as described in Example 2. Individual phages were isolated and DNA sequences were obtained using standard molecular biology methods described above.

After four rounds of phage display on CNT-7 with the graphite-cleaned library (round 4 with 0.5% concentration of Tween-20®), two consensus sequences emerged. These are:

```
HHHHLRHPFWTH       (SEQ ID NO: 23)
and

WPHHPHAAHTIR       (SEQ ID NO: 24)
```

The implication is that the binding of these sequences is specific to the CNT-7, as compared to a graphitic clone. The significance of the finding is in the close relationship between the graphene sheet that bounds freshly cleaved graphite, and the surface of carbon nanotubes. Carbon nanotube surfaces are essentially curved or graphene sheets. As such, objects may bind both to carbon nanotubes and to graphite. Additional significance may be attached to those whose binding discriminates between the two. This result illustrates that peptides can recognize different allotropes of carbon.

Example 6

Peptide Facilitated Binding of CNT to Microspheres

Example 6 illustrates that microspheres coated with CNT binding peptides are effective in binding single walled nanotubes and forcing assembly of the microspheres.

Preparation of Phage-Coated Microspheres.

Purified phage clones were amplified. Anti-mouse antibody IgG-coated microspheres (seven microns in diameter from Bangs Laboratories, Inc, 9025 Technology Drive, Fishers Ind. 46038-2886) were coated with an anti-M13 monoclonal antibody (Amersham pharmacia biotech Inc. 800 Centennial Avenue PO Box 1327 Piscataway N.J. 08855). Purified phage clones were coated onto these microspheres in TBS buffer. The phage-coated microspheres were incubated overnight with 10% Triton-X-165 dispersed SWNTs 7.5 µg/ml in a dialysis tube against 1 L of TBS buffer containing 10 grams of Amberlite XAD-4 (Sigma, P.O. Box 14508 ST. Louis, Mo. 63178). The microspheres were then washed three times with water. The beads were examined under SEM.

Preparation of Peptide-Coated Microspheres.

Selected sequences were synthesized as free peptides, including, NH$_2$-HWKHPWGAWDTLGGG-COOH (SEQ ID NO:25) and NH$_2$-HWKHPWGAWDTL-COOH (SEQ ID NO:13). Amino-modified microspheres (0.66 microns in diameter from Bangs Laboratories, Inc, 9025 Technology Drive, Fishers Ind. 46038-2886) were cross-linked to synthetic peptides at the C terminus through an EDC linker (Pierce Inc. 3747N. Meridian Road, P.O. Box 117, Rockford, Ill. 61105 Sigma, P.O. Box 14508 ST. Louis, Mo. 63178). The peptide-coated microspheres were incubated overnight with 10% Triton-X-165 dispersed SWNT 7.5 µg/ml in a dialysis tube against 1 L of TBS buffer containing 10 grams of Amberlite XAD-4. The microspheres were then washed three times with TBS buffer. The beads were examined under SEM.

Figure 3:
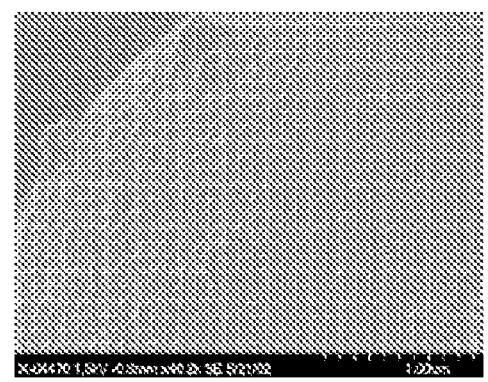
FIG. 3A is an electronmicrograph of a microsphere coated with a non-CNT binding control phage after exposure to SWNT.
FIG. 3B is an electronmicrograph of a microsphere coated with a CNT-binding phage after exposure to SWNT.
FIG. 3C is an electronmicrograph of a microsphere coated with a non-CNT binding peptide after exposure to SWNT.
FIG. 3D is an electronmicrograph of a microsphere coated with a CNT binding peptide after exposure to SWNT.
Figure 3:
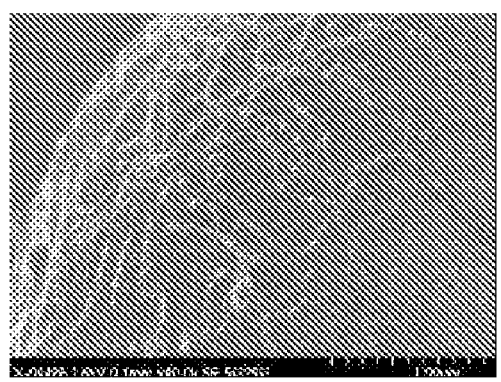
Figure 3:
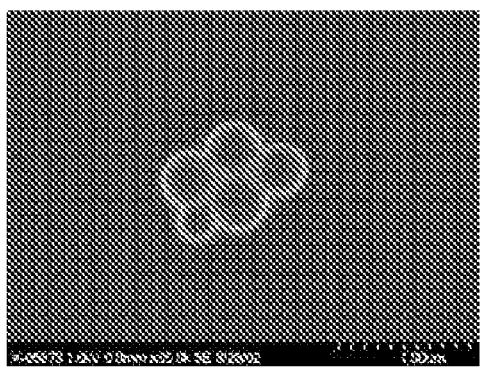
Figure 3:
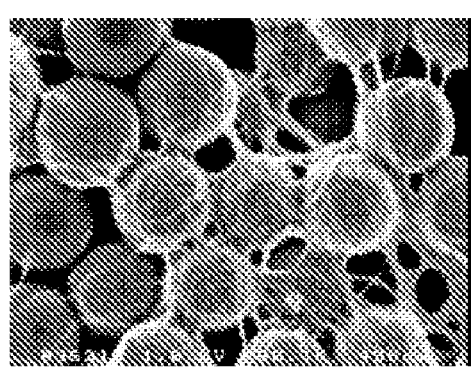

Results of contacting CNT's with microspheres either coated with CNT binding phage or isolated peptide are illustrated in FIG. 3a-d. FIG. 3(a) shows the surface of a microsphere coated with a control phage clone expressing peptide sequence NH$_2$-IDVESYKGTSMP-COOH. (SEQ ID NO:34). Clearly, there is no association of the carbon nanotubes with this surface. FIG. 3(b) shows the surface of a microsphere coated with the binding phage clone sequence NH$_2$-HWKHPWGAWDTL-COOH (SEQ ID NO:13). It demonstrates strong association between the phage and nanotube bundles. Similar results have been obtained with other nanotube-binding phage clones. FIG. 3(c), coated with the control peptide NH$_2$-LPPSNASVADYSGGG-COOH (SEQ ID NO:28), shows no association of microspheres with nanotubes. Indeed, the suspension of microspheres remained highly dispersed. FIG. 3(d) shows strong association between the microspheres coated with the binding peptide NH$_2$-HWKHPWGAWDTL-COOH (SEQ ID NO:13) and nanotubes. Essentially, the nanotubes cross-linked the microspheres, resulting in a loss of dispersion of the microspheres and formation of large clusters of microspheres.

Example 7

CMBP Generated to a Variety of Carbon Nanotube Substrates

This example illustrates that carbon nanotube binding peptides may be generated to a variety of carbon nanotube substrates including those made by the HiPCo process and those that have undergone various cleaning processes.

A series of experiments to select carbon nanotube binding peptides were performed as described in Example 2. The first substrate used was SWNTs from CNI prepared using the HiPCo process that was prepared only by acid cleaning, dispersion in toluene and drying to form a mat. Peptides resulting after the selection process are listed in SEQ. ID Nos:39-85.

The second substrate used in the selection process as described in Example 2 were MWNTs obtained from Yet-Ming Chiang, Department of Materials Science, MIT, Cambridge, Mass. Peptides that were selected are listed in SEQ. ID Nos:1-4, 6, 8, 10-13, 15, 16, 18-22, 28, 36, 92, 114-147, and 177. The above example was repeated used fresh MWNTs obtained from the same source. Resulting peptides are listed in SEQ. ID Nos:94-113 and 177.

Graphite-cleaned MWNTs obtained from Yet-Ming Chiang, Department of Materials Science, MIT, Cambridge, Mass. prepared as described in Example 5 and were also used as substrates. Resulting peptides are listed in SEQ. ID Nos: 148-176.

What is claimed is:

1. A composition comprising a solid substrate coated with a peptide having an amino acid sequence selected from the group consisting of SEQ ID Nos: 115-121, 123, 125 and 126.

2. The composition according to claim 1 wherein the peptide is affixed on a phage.

3. The composition according to claim 1 further comprising at least one carbon nanotube bound thereto.

* * * * *

SEQUENCE LISTING

<160> NUMBER OF SEQ ID NOS: 177

<210> SEQ ID NO 1
<211> LENGTH: 12
<212> TYPE: PRT
<213> ORGANISM: artificial sequence
<220> FEATURE:
<223> OTHER INFORMATION: generated by phage display

<400> SEQUENCE: 1

Asp Pro His His His Trp Tyr His Met His Gln His
1               5                   10

<210> SEQ ID NO 2
<211> LENGTH: 12
<212> TYPE: PRT
<213> ORGANISM: artificial sequence
<220> FEATURE:
<223> OTHER INFORMATION: generated by phage display

<400> SEQUENCE: 2

His Ala His Ser Gln Trp Trp His Leu Pro Tyr Arg
1               5                   10

<210> SEQ ID NO 3
<211> LENGTH: 12
<212> TYPE: PRT
<213> ORGANISM: artificial sequence
<220> FEATURE:
<223> OTHER INFORMATION: generated by phage display

<400> SEQUENCE: 3

His Ala His Ser Arg Arg Gly His Ile Gln His Arg
1               5                   10

<210> SEQ ID NO 4
<211> LENGTH: 12
<212> TYPE: PRT
<213> ORGANISM: artificial sequence
<220> FEATURE:
<223> OTHER INFORMATION: generated by phage display

<400> SEQUENCE: 4

His Cys His His Pro Trp Gly Ala Trp His Thr Leu
1               5                   10

<210> SEQ ID NO 5
<211> LENGTH: 12
<212> TYPE: PRT
<213> ORGANISM: artificial sequence
<220> FEATURE:
<223> OTHER INFORMATION: generated by phage display

<400> SEQUENCE: 5

His Cys Trp Asn Gln Trp Cys Ser Arg His Gln Thr
1               5                   10

<210> SEQ ID NO 6
<211> LENGTH: 12
<212> TYPE: PRT
<213> ORGANISM: artificial sequence
<220> FEATURE:
<223> OTHER INFORMATION: generated by phage display

<400> SEQUENCE: 6

His Gly Asn Trp Ser Tyr Trp Trp Ser Lys Pro Ser

<210> SEQ ID NO 7
<211> LENGTH: 12
<212> TYPE: PRT
<213> ORGANISM: artificial sequence
<220> FEATURE:
<223> OTHER INFORMATION: generated by phage display

<400> SEQUENCE: 7

His His Trp His His Trp Cys Met Pro His Lys Thr
1               5                   10

<210> SEQ ID NO 8
<211> LENGTH: 12
<212> TYPE: PRT
<213> ORGANISM: artificial sequence
<220> FEATURE:
<223> OTHER INFORMATION: generated by phage display

<400> SEQUENCE: 8

His Asn Trp Tyr His Trp Trp Met Pro His Asn Thr
1               5                   10

<210> SEQ ID NO 9
<211> LENGTH: 12
<212> TYPE: PRT
<213> ORGANISM: artificial sequence
<220> FEATURE:
<223> OTHER INFORMATION: generated by phage display

<400> SEQUENCE: 9

His Asn Trp Tyr Arg Trp Cys Ile Arg His Asn Asn
1               5                   10

<210> SEQ ID NO 10
<211> LENGTH: 12
<212> TYPE: PRT
<213> ORGANISM: artificial sequence
<220> FEATURE:
<223> OTHER INFORMATION: generated by phage display

<400> SEQUENCE: 10

His Arg Trp Tyr Arg Trp Ser Ser Arg Asn Gln Thr
1               5                   10

<210> SEQ ID NO 11
<211> LENGTH: 12
<212> TYPE: PRT
<213> ORGANISM: artificial sequence
<220> FEATURE:
<223> OTHER INFORMATION: generated by phage display

<400> SEQUENCE: 11

His Ser Ser Trp Trp Leu Ala Leu Ala Lys Pro Thr
1               5                   10

<210> SEQ ID NO 12
<211> LENGTH: 12
<212> TYPE: PRT
<213> ORGANISM: artificial sequence
<220> FEATURE:
<223> OTHER INFORMATION: generated by phage display

<400> SEQUENCE: 12

His Trp Cys Ala Trp Trp Ile Ser Ser Asn Gln Ser
1               5                   10

```
<210> SEQ ID NO 13
<211> LENGTH: 12
<212> TYPE: PRT
<213> ORGANISM: artificial sequence
<220> FEATURE:
<223> OTHER INFORMATION: generated by phage display

<400> SEQUENCE: 13

His Trp Lys His Pro Trp Gly Ala Trp Asp Thr Leu
1               5                   10

<210> SEQ ID NO 14
<211> LENGTH: 12
<212> TYPE: PRT
<213> ORGANISM: artificial sequence
<220> FEATURE:
<223> OTHER INFORMATION: generated by phage display

<400> SEQUENCE: 14

His Trp Ser Ala Trp Trp Ile Arg Ser Asn Gln Ser
1               5                   10

<210> SEQ ID NO 15
<211> LENGTH: 12
<212> TYPE: PRT
<213> ORGANISM: artificial sequence
<220> FEATURE:
<223> OTHER INFORMATION: generated by phage display

<400> SEQUENCE: 15

His Trp Ser Pro Trp His Arg Pro Trp Tyr Gln Pro
1               5                   10

<210> SEQ ID NO 16
<211> LENGTH: 12
<212> TYPE: PRT
<213> ORGANISM: artificial sequence
<220> FEATURE:
<223> OTHER INFORMATION: generated by phage display

<400> SEQUENCE: 16

His Tyr Ser Trp Tyr Ser Thr Trp Trp Pro Pro Val
1               5                   10

<210> SEQ ID NO 17
<211> LENGTH: 12
<212> TYPE: PRT
<213> ORGANISM: artificial sequence
<220> FEATURE:
<223> OTHER INFORMATION: generated by phage display

<400> SEQUENCE: 17

His Tyr Trp Trp Arg Trp Trp Met Pro Asn Gln Thr
1               5                   10

<210> SEQ ID NO 18
<211> LENGTH: 12
<212> TYPE: PRT
<213> ORGANISM: artificial sequence
<220> FEATURE:
<223> OTHER INFORMATION: generated by phage display

<400> SEQUENCE: 18

Lys Cys His Ser Arg His Asp His Ile His His His
1               5                   10

<210> SEQ ID NO 19
```

```
<211> LENGTH: 12
<212> TYPE: PRT
<213> ORGANISM: artificial sequence
<220> FEATURE:
<223> OTHER INFORMATION: generated by phage display

<400> SEQUENCE: 19

Lys Ser Leu Ser Arg His Asp His Ile His His His
1               5                   10

<210> SEQ ID NO 20
<211> LENGTH: 12
<212> TYPE: PRT
<213> ORGANISM: artificial sequence
<220> FEATURE:
<223> OTHER INFORMATION: generated by phage display

<400> SEQUENCE: 20

Lys Ser Arg Ser Arg His Asp Glu Ile His His His
1               5                   10

<210> SEQ ID NO 21
<211> LENGTH: 12
<212> TYPE: PRT
<213> ORGANISM: artificial sequence
<220> FEATURE:
<223> OTHER INFORMATION: generated by phage display

<400> SEQUENCE: 21

Lys Tyr Arg Ser Arg His Asp His Ile His His His
1               5                   10

<210> SEQ ID NO 22
<211> LENGTH: 12
<212> TYPE: PRT
<213> ORGANISM: artificial sequence
<220> FEATURE:
<223> OTHER INFORMATION: generated by phage display

<400> SEQUENCE: 22

Gln Trp His Ser Arg His Asp His Ile His His His
1               5                   10

<210> SEQ ID NO 23
<211> LENGTH: 12
<212> TYPE: PRT
<213> ORGANISM: artificial sequence
<220> FEATURE:
<223> OTHER INFORMATION: generated by phage display

<400> SEQUENCE: 23

His His His His Leu Arg His Pro Phe Trp Thr His
1               5                   10

<210> SEQ ID NO 24
<211> LENGTH: 12
<212> TYPE: PRT
<213> ORGANISM: artificial sequence
<220> FEATURE:
<223> OTHER INFORMATION: generated by phage display

<400> SEQUENCE: 24

Trp Pro His His Pro His Ala Ala His Thr Ile Arg
1               5                   10

<210> SEQ ID NO 25
<211> LENGTH: 15
<212> TYPE: PRT
```

```
<213> ORGANISM: artificial sequence
<220> FEATURE:
<223> OTHER INFORMATION: generated by phage display

<400> SEQUENCE: 25

His Trp Lys His Pro Trp Gly Ala Trp Asp Thr Leu Gly Gly Gly
1               5                   10                  15

<210> SEQ ID NO 26
<211> LENGTH: 12
<212> TYPE: PRT
<213> ORGANISM: artificial sequence
<220> FEATURE:
<223> OTHER INFORMATION: generated by phage display

<400> SEQUENCE: 26

His Trp Lys His Pro Ser Gly Ala Trp Asp Thr Leu
1               5                   10

<210> SEQ ID NO 27
<211> LENGTH: 12
<212> TYPE: PRT
<213> ORGANISM: artificial sequence
<220> FEATURE:
<223> OTHER INFORMATION: generated by phage display

<400> SEQUENCE: 27

His Trp Ser Ala Trp Ser Ile Arg Ser Asn Gln Ser
1               5                   10

<210> SEQ ID NO 28
<211> LENGTH: 12
<212> TYPE: PRT
<213> ORGANISM: artificial sequence
<220> FEATURE:
<223> OTHER INFORMATION: generated by phage display

<400> SEQUENCE: 28

Leu Pro Pro Ser Asn Ala Ser Val Ala Asp Tyr Ser
1               5                   10

<210> SEQ ID NO 29
<211> LENGTH: 7
<212> TYPE: PRT
<213> ORGANISM: artificial sequence
<220> FEATURE:
<223> OTHER INFORMATION: generated by phage display

<400> SEQUENCE: 29

Arg Lys His Tyr Cys Asp Glu
1               5

<210> SEQ ID NO 30
<211> LENGTH: 6
<212> TYPE: PRT
<213> ORGANISM: artificial sequence
<220> FEATURE:
<223> OTHER INFORMATION: generated by phage display

<400> SEQUENCE: 30

Asn Cys Gln Ser Thr Tyr
1               5

<210> SEQ ID NO 31
<211> LENGTH: 5
<212> TYPE: PRT
<213> ORGANISM: artificial sequence
<220> FEATURE:
```

<223> OTHER INFORMATION: generated by phage display

<400> SEQUENCE: 31

Ala Ile Leu Phe Trp
1               5

<210> SEQ ID NO 32
<211> LENGTH: 15
<212> TYPE: PRT
<213> ORGANISM: artificial sequence
<220> FEATURE:
<223> OTHER INFORMATION: generated by phage display

<400> SEQUENCE: 32

His Trp Lys His Pro Ser Gly Ala Trp Asp Thr Leu Gly Gly Gly
1               5                   10                  15

<210> SEQ ID NO 33
<211> LENGTH: 20
<212> TYPE: PRT
<213> ORGANISM: artificial sequence
<220> FEATURE:
<223> OTHER INFORMATION: generated by phage display

<400> SEQUENCE: 33

Cys Cys Cys Thr Cys Ala Thr Ala Gly Thr Thr Ala Gly Cys Gly Thr
1               5                   10                  15

Ala Ala Cys Gly
            20

<210> SEQ ID NO 34
<211> LENGTH: 12
<212> TYPE: PRT
<213> ORGANISM: artificial sequence
<220> FEATURE:
<223> OTHER INFORMATION: generated by phage display

<400> SEQUENCE: 34

Ile Asp Val Glu Ser Tyr Lys Gly Thr Ser Met Pro
1               5                   10

<210> SEQ ID NO 35
<211> LENGTH: 11
<212> TYPE: PRT
<213> ORGANISM: artificial sequence
<220> FEATURE:
<223> OTHER INFORMATION: generated by phage display

<400> SEQUENCE: 35

His Asn Trp Tyr His Trp Trp Pro His Asn Thr
1               5                   10

<210> SEQ ID NO 36
<211> LENGTH: 12
<212> TYPE: PRT
<213> ORGANISM: artificial sequence
<220> FEATURE:
<223> OTHER INFORMATION: generated by phage display

<400> SEQUENCE: 36

His Trp Tyr Lys Pro Tyr His Phe Gln Ser Leu Thr
1               5                   10

<210> SEQ ID NO 37
<211> LENGTH: 12
<212> TYPE: PRT
<213> ORGANISM: artificial sequence

```
<220> FEATURE:
<223> OTHER INFORMATION: generated by phage display

<400> SEQUENCE: 37

Ser Val Ser Val Gly Met Lys Pro Ser Pro Arg Pro
1               5                   10

<210> SEQ ID NO 38
<211> LENGTH: 12
<212> TYPE: PRT
<213> ORGANISM: artificial sequence
<220> FEATURE:
<223> OTHER INFORMATION: generated by phage display

<400> SEQUENCE: 38

Glu Ala His Pro Gln Thr Leu Gly Trp Gln Arg Pro
1               5                   10

<210> SEQ ID NO 39
<211> LENGTH: 12
<212> TYPE: PRT
<213> ORGANISM: artificial sequence
<220> FEATURE:
<223> OTHER INFORMATION: generated by phage display

<400> SEQUENCE: 39

His Asn Ala Tyr Trp His Trp Pro Pro Ser Met Thr
1               5                   10

<210> SEQ ID NO 40
<211> LENGTH: 12
<212> TYPE: PRT
<213> ORGANISM: Artificial sequence
<220> FEATURE:
<223> OTHER INFORMATION: generated by phage display

<400> SEQUENCE: 40

Ala Glu Pro Trp Ala Ser Val Ser Thr Pro Pro Pro
1               5                   10

<210> SEQ ID NO 41
<211> LENGTH: 12
<212> TYPE: PRT
<213> ORGANISM: Artificial sequence
<220> FEATURE:
<223> OTHER INFORMATION: generated by phage display

<400> SEQUENCE: 41

Ala His Arg Ser Asp Phe Trp Arg Pro Phe Pro Thr
1               5                   10

<210> SEQ ID NO 42
<211> LENGTH: 12
<212> TYPE: PRT
<213> ORGANISM: Artificial sequence
<220> FEATURE:
<223> OTHER INFORMATION: generated by phage display

<400> SEQUENCE: 42

Ala Leu Pro Arg Asn Asp Leu Ser Asp Ala Ala Ser
1               5                   10

<210> SEQ ID NO 43
<211> LENGTH: 12
<212> TYPE: PRT
<213> ORGANISM: Artificial sequence
<220> FEATURE:
<223> OTHER INFORMATION: generated by phage display
```

```
<400> SEQUENCE: 43

Ala Thr Ser Thr Phe Trp Pro Arg Ala Phe Pro Ala
1               5                   10

<210> SEQ ID NO 44
<211> LENGTH: 12
<212> TYPE: PRT
<213> ORGANISM: Artificial sequence
<220> FEATURE:
<223> OTHER INFORMATION: generated by phage display

<400> SEQUENCE: 44

Asp Arg Val Pro Ile Gln Pro Trp Thr Ala Pro Arg
1               5                   10

<210> SEQ ID NO 45
<211> LENGTH: 12
<212> TYPE: PRT
<213> ORGANISM: Artificial sequence
<220> FEATURE:
<223> OTHER INFORMATION: generated by phage display

<400> SEQUENCE: 45

Phe Gly Asn Ser Asp Lys Leu Gln Thr Arg Ala Phe
1               5                   10

<210> SEQ ID NO 46
<211> LENGTH: 12
<212> TYPE: PRT
<213> ORGANISM: Artificial sequence
<220> FEATURE:
<223> OTHER INFORMATION: generated by phage display

<400> SEQUENCE: 46

Phe His Lys Ala Pro Lys Ser Pro Gly Met Pro Thr
1               5                   10

<210> SEQ ID NO 47
<211> LENGTH: 12
<212> TYPE: PRT
<213> ORGANISM: Artificial sequence
<220> FEATURE:
<223> OTHER INFORMATION: generated by phage display

<400> SEQUENCE: 47

Phe His Arg His Gln Glu Met Thr Ala Thr Val His
1               5                   10

<210> SEQ ID NO 48
<211> LENGTH: 12
<212> TYPE: PRT
<213> ORGANISM: Artificial sequence
<220> FEATURE:
<223> OTHER INFORMATION: generated by phage display

<400> SEQUENCE: 48

Phe Pro Leu Arg Pro Val Glu Val Lys Asp Ala Ser
1               5                   10

<210> SEQ ID NO 49
<211> LENGTH: 12
<212> TYPE: PRT
<213> ORGANISM: Artificial sequence
<220> FEATURE:
<223> OTHER INFORMATION: generated by phage display

<400> SEQUENCE: 49
```

```
Gly Leu Pro Glu Met Arg Leu Pro Leu Val Pro Pro
1               5                   10
```

<210> SEQ ID NO 50
<211> LENGTH: 12
<212> TYPE: PRT
<213> ORGANISM: Artificial sequence
<220> FEATURE:
<223> OTHER INFORMATION: generated by phage display

<400> SEQUENCE: 50

```
Gly Gln Thr Ile Pro Val Asp Lys Thr Gln Ser Pro
1               5                   10
```

<210> SEQ ID NO 51
<211> LENGTH: 12
<212> TYPE: PRT
<213> ORGANISM: Artificial sequence
<220> FEATURE:
<223> OTHER INFORMATION: generated by phage display

<400> SEQUENCE: 51

```
His Ala His Ser Trp Pro Pro Ala His Gln Leu His
1               5                   10
```

<210> SEQ ID NO 52
<211> LENGTH: 12
<212> TYPE: PRT
<213> ORGANISM: Artificial sequence
<220> FEATURE:
<223> OTHER INFORMATION: generated by phage display

<400> SEQUENCE: 52

```
His Phe Pro Leu Ser Ser Asn Lys Val Pro Arg Ala
1               5                   10
```

<210> SEQ ID NO 53
<211> LENGTH: 12
<212> TYPE: PRT
<213> ORGANISM: Artificial sequence
<220> FEATURE:
<223> OTHER INFORMATION: generated by phage display

<400> SEQUENCE: 53

```
His Phe Ser Ser Thr Leu Ser Leu Gln Glu Leu Asp
1               5                   10
```

<210> SEQ ID NO 54
<211> LENGTH: 12
<212> TYPE: PRT
<213> ORGANISM: Artificial sequence
<220> FEATURE:
<223> OTHER INFORMATION: generated by phage display

<400> SEQUENCE: 54

```
His Ile Lys Ile Gln Pro Arg Ala Pro Val Phe Met
1               5                   10
```

<210> SEQ ID NO 55
<211> LENGTH: 12
<212> TYPE: PRT
<213> ORGANISM: Artificial sequence
<220> FEATURE:
<223> OTHER INFORMATION: generated by phage display

<400> SEQUENCE: 55

```
His Lys Pro His Leu Tyr Asn Lys Pro Thr Phe Thr
```

<210> SEQ ID NO 56
<211> LENGTH: 12
<212> TYPE: PRT
<213> ORGANISM: Artificial sequence
<220> FEATURE:
<223> OTHER INFORMATION: generated by phage display

<400> SEQUENCE: 56

His Leu Lys Met Pro Lys Phe Ala His Pro Asn Leu
1               5                   10

<210> SEQ ID NO 57
<211> LENGTH: 12
<212> TYPE: PRT
<213> ORGANISM: Artificial sequence
<220> FEATURE:
<223> OTHER INFORMATION: generated by phage display

<400> SEQUENCE: 57

His Leu Pro Met Thr Tyr Ser Ala Thr Asn Pro Val
1               5                   10

<210> SEQ ID NO 58
<211> LENGTH: 12
<212> TYPE: PRT
<213> ORGANISM: Artificial sequence
<220> FEATURE:
<223> OTHER INFORMATION: generated by phage display

<400> SEQUENCE: 58

His Asn Lys Pro His His Phe Pro Arg Leu Leu Thr
1               5                   10

<210> SEQ ID NO 59
<211> LENGTH: 12
<212> TYPE: PRT
<213> ORGANISM: Artificial sequence
<220> FEATURE:
<223> OTHER INFORMATION: generated by phage display

<400> SEQUENCE: 59

His Pro Met Val Glu Asn Thr Val Ser Ser Trp Thr
1               5                   10

<210> SEQ ID NO 60
<211> LENGTH: 12
<212> TYPE: PRT
<213> ORGANISM: Artificial sequence
<220> FEATURE:
<223> OTHER INFORMATION: generated by phage display

<400> SEQUENCE: 60

His Pro Thr Gln Lys Asn Val His Pro Phe Arg Ser
1               5                   10

<210> SEQ ID NO 61
<211> LENGTH: 12
<212> TYPE: PRT
<213> ORGANISM: Artificial sequence
<220> FEATURE:
<223> OTHER INFORMATION: generated by phage display

<400> SEQUENCE: 61

His Ser Ser Pro His Phe Ser Arg His Gly Leu Leu
1               5                   10

<210> SEQ ID NO 62
<211> LENGTH: 12
<212> TYPE: PRT
<213> ORGANISM: Artificial sequence
<220> FEATURE:
<223> OTHER INFORMATION: generated by phage display

<400> SEQUENCE: 62

His Thr Ile Pro Thr Ile Ser Thr His Phe Trp Asp
1               5                   10

<210> SEQ ID NO 63
<211> LENGTH: 12
<212> TYPE: PRT
<213> ORGANISM: Artificial sequence
<220> FEATURE:
<223> OTHER INFORMATION: generated by phage display

<400> SEQUENCE: 63

His Thr Lys Gln Ile Pro Arg His Ile Tyr Ser Ala
1               5                   10

<210> SEQ ID NO 64
<211> LENGTH: 12
<212> TYPE: PRT
<213> ORGANISM: Artificial sequence
<220> FEATURE:
<223> OTHER INFORMATION: generated by phage display

<400> SEQUENCE: 64

Lys Thr Leu Tyr Leu Pro Asn Ser Leu Arg Leu His
1               5                   10

<210> SEQ ID NO 65
<211> LENGTH: 12
<212> TYPE: PRT
<213> ORGANISM: Artificial sequence
<220> FEATURE:
<223> OTHER INFORMATION: generated by phage display

<400> SEQUENCE: 65

Lys Tyr Gly Asp Pro Leu Ser Leu Thr Trp Gly Arg
1               5                   10

<210> SEQ ID NO 66
<211> LENGTH: 12
<212> TYPE: PRT
<213> ORGANISM: Artificial sequence
<220> FEATURE:
<223> OTHER INFORMATION: generated by phage display

<400> SEQUENCE: 66

Met His Arg Ser Asp Leu Met Ser Ala Ala Val Arg
1               5                   10

<210> SEQ ID NO 67
<211> LENGTH: 12
<212> TYPE: PRT
<213> ORGANISM: Artificial sequence
<220> FEATURE:
<223> OTHER INFORMATION: generated by phage display

<400> SEQUENCE: 67

Met Pro Lys Leu Met Thr Met Asp Lys Ser Met Tyr
1               5                   10

<210> SEQ ID NO 68

```
<211> LENGTH: 12
<212> TYPE: PRT
<213> ORGANISM: Artificial sequence
<220> FEATURE:
<223> OTHER INFORMATION: generated by phage display

<400> SEQUENCE: 68

Asn Thr Lys Ser Trp Ala Ala Pro Ala Pro Glu Tyr
1               5                   10

<210> SEQ ID NO 69
<211> LENGTH: 12
<212> TYPE: PRT
<213> ORGANISM: Artificial sequence
<220> FEATURE:
<223> OTHER INFORMATION: generated by phage display

<400> SEQUENCE: 69

Gln Gln Asn Val Ala Leu Arg Leu Asp Trp Met Gly
1               5                   10

<210> SEQ ID NO 70
<211> LENGTH: 12
<212> TYPE: PRT
<213> ORGANISM: Artificial sequence
<220> FEATURE:
<223> OTHER INFORMATION: generated by phage display

<400> SEQUENCE: 70

Gln Thr Ile Thr Ser Pro Gln Met His Pro Arg Ala
1               5                   10

<210> SEQ ID NO 71
<211> LENGTH: 12
<212> TYPE: PRT
<213> ORGANISM: Artificial sequence
<220> FEATURE:
<223> OTHER INFORMATION: generated by phage display

<400> SEQUENCE: 71

Ser Pro Thr Trp Ser Gln Ser Lys Asn Ser Asn Gln
1               5                   10

<210> SEQ ID NO 72
<211> LENGTH: 12
<212> TYPE: PRT
<213> ORGANISM: Artificial sequence
<220> FEATURE:
<223> OTHER INFORMATION: generated by phage display

<400> SEQUENCE: 72

Ser Arg Tyr Ile Pro Asp Phe Ala Thr Ser Ala Pro
1               5                   10

<210> SEQ ID NO 73
<211> LENGTH: 12
<212> TYPE: PRT
<213> ORGANISM: Artificial sequence
<220> FEATURE:
<223> OTHER INFORMATION: generated by phage display

<400> SEQUENCE: 73

Ser Ser Pro Leu Pro Leu Ser Met Ser Ala Pro Arg
1               5                   10

<210> SEQ ID NO 74
<211> LENGTH: 12
<212> TYPE: PRT
```

```
<213> ORGANISM: Artificial sequence
<220> FEATURE:
<223> OTHER INFORMATION: generated by phage display

<400> SEQUENCE: 74

Ser Ser Trp Asn Glu Ala Tyr Arg Ser Arg Ser Gly
1               5                   10

<210> SEQ ID NO 75
<211> LENGTH: 12
<212> TYPE: PRT
<213> ORGANISM: Artificial sequence
<220> FEATURE:
<223> OTHER INFORMATION: generated by phage display

<400> SEQUENCE: 75

Ser Tyr Thr Phe His Gln Leu Pro Ser Ala His Leu
1               5                   10

<210> SEQ ID NO 76
<211> LENGTH: 12
<212> TYPE: PRT
<213> ORGANISM: Artificial sequence
<220> FEATURE:
<223> OTHER INFORMATION: generated by phage display

<400> SEQUENCE: 76

Thr Phe Ser Asn Leu Gln Thr Thr Ala Gln Ala Val
1               5                   10

<210> SEQ ID NO 77
<211> LENGTH: 12
<212> TYPE: PRT
<213> ORGANISM: Artificial sequence
<220> FEATURE:
<223> OTHER INFORMATION: generated by phage display

<400> SEQUENCE: 77

Thr His Ile Leu Thr Lys Ser Ala Ser Ser Tyr Ile
1               5                   10

<210> SEQ ID NO 78
<211> LENGTH: 12
<212> TYPE: PRT
<213> ORGANISM: Artificial sequence
<220> FEATURE:
<223> OTHER INFORMATION: generated by phage display

<400> SEQUENCE: 78

Thr His Pro Trp Ser Leu Lys Thr Thr Ser Phe Ser
1               5                   10

<210> SEQ ID NO 79
<211> LENGTH: 12
<212> TYPE: PRT
<213> ORGANISM: Artificial sequence
<220> FEATURE:
<223> OTHER INFORMATION: generated by phage display

<400> SEQUENCE: 79

Thr Thr His Leu His Thr Asp Ser Asp Leu Gly Arg
1               5                   10

<210> SEQ ID NO 80
<211> LENGTH: 12
<212> TYPE: PRT
<213> ORGANISM: Artificial sequence
<220> FEATURE:
```

<223> OTHER INFORMATION: generated by phage display

<400> SEQUENCE: 80

Thr Thr Ile Ile Ser Lys Asn His Ala Thr Ser Thr
1               5                   10

<210> SEQ ID NO 81
<211> LENGTH: 12
<212> TYPE: PRT
<213> ORGANISM: Artificial sequence
<220> FEATURE:
<223> OTHER INFORMATION: generated by phage display

<400> SEQUENCE: 81

Val Ala Pro Tyr Asn Ile Thr Ser Pro Trp Thr Ser
1               5                   10

<210> SEQ ID NO 82
<211> LENGTH: 12
<212> TYPE: PRT
<213> ORGANISM: Artificial sequence
<220> FEATURE:
<223> OTHER INFORMATION: generated by phage display

<400> SEQUENCE: 82

Trp Pro His Tyr His Pro Arg Ser Thr Ile Lys Thr
1               5                   10

<210> SEQ ID NO 83
<211> LENGTH: 12
<212> TYPE: PRT
<213> ORGANISM: Artificial sequence
<220> FEATURE:
<223> OTHER INFORMATION: generated by phage display

<400> SEQUENCE: 83

Tyr Gly Gln Asn Thr Thr Ser Pro Pro Tyr Leu Ser
1               5                   10

<210> SEQ ID NO 84
<211> LENGTH: 12
<212> TYPE: PRT
<213> ORGANISM: Artificial sequence
<220> FEATURE:
<223> OTHER INFORMATION: generated by phage display

<400> SEQUENCE: 84

Tyr Gln Thr Asn Ser Tyr Asn Ala Thr Pro Ala Leu
1               5                   10

<210> SEQ ID NO 85
<211> LENGTH: 12
<212> TYPE: PRT
<213> ORGANISM: Artificial sequence
<220> FEATURE:
<223> OTHER INFORMATION: generated by phage display

<400> SEQUENCE: 85

Tyr Val Ser Val Gly Met Lys Pro Ser Pro Arg Pro
1               5                   10

<210> SEQ ID NO 86
<211> LENGTH: 12
<212> TYPE: PRT
<213> ORGANISM: Artificial sequence
<220> FEATURE:
<223> OTHER INFORMATION: generated by phage display

```
<400> SEQUENCE: 86

Ala Asn Arg Ala Leu Leu Leu Asn Asp His Pro Met
1               5                   10

<210> SEQ ID NO 87
<211> LENGTH: 12
<212> TYPE: PRT
<213> ORGANISM: Artificial sequence
<220> FEATURE:
<223> OTHER INFORMATION: generated by phage display

<400> SEQUENCE: 87

Ala Pro Ala Gly His Cys Ser Val Cys Ser Arg Ile
1               5                   10

<210> SEQ ID NO 88
<211> LENGTH: 12
<212> TYPE: PRT
<213> ORGANISM: Artificial sequence
<220> FEATURE:
<223> OTHER INFORMATION: generated by phage display

<400> SEQUENCE: 88

Ala Pro Asp Val Thr Lys Val Arg Thr Lys Asp Thr
1               5                   10

<210> SEQ ID NO 89
<211> LENGTH: 12
<212> TYPE: PRT
<213> ORGANISM: Artificial sequence
<220> FEATURE:
<223> OTHER INFORMATION: generated by phage display

<400> SEQUENCE: 89

Asp His Trp His His Trp Cys Asn Leu His Lys Pro
1               5                   10

<210> SEQ ID NO 90
<211> LENGTH: 12
<212> TYPE: PRT
<213> ORGANISM: Artificial sequence
<220> FEATURE:
<223> OTHER INFORMATION: generated by phage display

<400> SEQUENCE: 90

Glu His Arg Asn Gln Trp Cys Ile His Asp Lys Arg
1               5                   10

<210> SEQ ID NO 91
<211> LENGTH: 12
<212> TYPE: PRT
<213> ORGANISM: Artificial sequence
<220> FEATURE:
<223> OTHER INFORMATION: generated by phage display

<400> SEQUENCE: 91

Glu Tyr Leu Ser Ala Ile Val Ala Gly Pro Trp Pro
1               5                   10

<210> SEQ ID NO 92
<211> LENGTH: 12
<212> TYPE: PRT
<213> ORGANISM: Artificial sequence
<220> FEATURE:
<223> OTHER INFORMATION: generated by phage display

<400> SEQUENCE: 92
```

-continued

```
Gly Pro His His Tyr Trp Tyr His Leu Arg Leu Pro
1               5                   10

<210> SEQ ID NO 93
<211> LENGTH: 12
<212> TYPE: PRT
<213> ORGANISM: Artificial sequence
<220> FEATURE:
<223> OTHER INFORMATION: generated by phage display

<400> SEQUENCE: 93

His Gly Val Trp Thr Pro Trp Met Tyr Ser Phe Ser
1               5                   10

<210> SEQ ID NO 94
<211> LENGTH: 12
<212> TYPE: PRT
<213> ORGANISM: Artificial sequence
<220> FEATURE:
<223> OTHER INFORMATION: generated by phage display

<400> SEQUENCE: 94

His Lys Arg His His Tyr Arg Gln Ala Cys Met His
1               5                   10

<210> SEQ ID NO 95
<211> LENGTH: 12
<212> TYPE: PRT
<213> ORGANISM: Artificial sequence
<220> FEATURE:
<223> OTHER INFORMATION: generated by phage display

<400> SEQUENCE: 95

His Asn Trp Trp Pro Ser Trp Pro Pro Gly Pro Ser
1               5                   10

<210> SEQ ID NO 96
<211> LENGTH: 12
<212> TYPE: PRT
<213> ORGANISM: Artificial sequence
<220> FEATURE:
<223> OTHER INFORMATION: generated by phage display

<400> SEQUENCE: 96

His Asn Trp Tyr His Trp Trp Met Leu Asp Asn Asn
1               5                   10

<210> SEQ ID NO 97
<211> LENGTH: 12
<212> TYPE: PRT
<213> ORGANISM: Artificial sequence
<220> FEATURE:
<223> OTHER INFORMATION: generated by phage display

<400> SEQUENCE: 97

His Asn Tyr Arg Ile Trp Asn His Trp Trp Leu Ser
1               5                   10

<210> SEQ ID NO 98
<211> LENGTH: 12
<212> TYPE: PRT
<213> ORGANISM: Artificial sequence
<220> FEATURE:
<223> OTHER INFORMATION: generated by phage display

<400> SEQUENCE: 98

His Thr Thr Trp Pro Arg Trp Trp Ala Ser Phe Ser
1               5                   10
```

```
<210> SEQ ID NO 99
<211> LENGTH: 12
<212> TYPE: PRT
<213> ORGANISM: Artificial sequence
<220> FEATURE:
<223> OTHER INFORMATION: generated by phage display

<400> SEQUENCE: 99

His Val Trp Glu Arg Arg Arg Thr Arg His Asn Pro
1               5                   10

<210> SEQ ID NO 100
<211> LENGTH: 12
<212> TYPE: PRT
<213> ORGANISM: Artificial sequence
<220> FEATURE:
<223> OTHER INFORMATION: generated by phage display

<400> SEQUENCE: 100

His Trp Arg Pro Trp Gln His Val Ser Ser Phe Leu
1               5                   10

<210> SEQ ID NO 101
<211> LENGTH: 12
<212> TYPE: PRT
<213> ORGANISM: Artificial sequence
<220> FEATURE:
<223> OTHER INFORMATION: generated by phage display

<400> SEQUENCE: 101

His Trp Thr His Phe Trp Thr Arg Thr Leu Pro His
1               5                   10

<210> SEQ ID NO 102
<211> LENGTH: 12
<212> TYPE: PRT
<213> ORGANISM: Artificial sequence
<220> FEATURE:
<223> OTHER INFORMATION: generated by phage display

<400> SEQUENCE: 102

His Trp Trp Thr Gly Ile Pro Thr Arg Tyr Leu Phe
1               5                   10

<210> SEQ ID NO 103
<211> LENGTH: 12
<212> TYPE: PRT
<213> ORGANISM: Artificial sequence
<220> FEATURE:
<223> OTHER INFORMATION: generated by phage display

<400> SEQUENCE: 103

His Tyr Trp Trp Trp Arg Ala Met Ala Lys Gln Thr
1               5                   10

<210> SEQ ID NO 104
<211> LENGTH: 12
<212> TYPE: PRT
<213> ORGANISM: Artificial sequence
<220> FEATURE:
<223> OTHER INFORMATION: generated by phage display

<400> SEQUENCE: 104

Lys Pro Ile Gln Tyr Asn Asn Gly Leu Gln Ala Phe
1               5                   10
```

```
<210> SEQ ID NO 105
<211> LENGTH: 12
<212> TYPE: PRT
<213> ORGANISM: Artificial sequence
<220> FEATURE:
<223> OTHER INFORMATION: generated by phage display

<400> SEQUENCE: 105

Lys Thr Phe His Ala Gly Asn Ser Asn His Leu Ala
1               5                   10

<210> SEQ ID NO 106
<211> LENGTH: 12
<212> TYPE: PRT
<213> ORGANISM: Artificial sequence
<220> FEATURE:
<223> OTHER INFORMATION: generated by phage display

<400> SEQUENCE: 106

Gln Ser Lys Ser His Asn Ser Phe Leu Asn Ser Pro
1               5                   10

<210> SEQ ID NO 107
<211> LENGTH: 12
<212> TYPE: PRT
<213> ORGANISM: Artificial sequence
<220> FEATURE:
<223> OTHER INFORMATION: generated by phage display

<400> SEQUENCE: 107

Ser Phe Ser Pro Gln Tyr Arg Ala Pro Gly Gln His
1               5                   10

<210> SEQ ID NO 108
<211> LENGTH: 12
<212> TYPE: PRT
<213> ORGANISM: Artificial sequence
<220> FEATURE:
<223> OTHER INFORMATION: generated by phage display

<400> SEQUENCE: 108

Ser Thr Asn Gln Ala Arg Phe Pro Leu His Ala Leu
1               5                   10

<210> SEQ ID NO 109
<211> LENGTH: 12
<212> TYPE: PRT
<213> ORGANISM: Artificial sequence
<220> FEATURE:
<223> OTHER INFORMATION: generated by phage display

<400> SEQUENCE: 109

Thr Pro Phe Leu Pro Asn Val Gly Thr Phe Ser Arg
1               5                   10

<210> SEQ ID NO 110
<211> LENGTH: 12
<212> TYPE: PRT
<213> ORGANISM: Artificial sequence
<220> FEATURE:
<223> OTHER INFORMATION: generated by phage display

<400> SEQUENCE: 110

Val Leu Pro His Lys Pro Met Arg Gln Pro Val Ala
1               5                   10

<210> SEQ ID NO 111
<211> LENGTH: 12
```

```
<212> TYPE: PRT
<213> ORGANISM: Artificial sequence
<220> FEATURE:
<223> OTHER INFORMATION: generated by phage display

<400> SEQUENCE: 111

Tyr Ala Ser Leu Ile Asn Pro Ile Leu Glu Pro Pro
1               5                   10

<210> SEQ ID NO 112
<211> LENGTH: 12
<212> TYPE: PRT
<213> ORGANISM: Artificial sequence
<220> FEATURE:
<223> OTHER INFORMATION: generated by phage display

<400> SEQUENCE: 112

Tyr His Lys Pro Phe Asn Tyr Ala Phe Pro Arg Thr
1               5                   10

<210> SEQ ID NO 113
<211> LENGTH: 12
<212> TYPE: PRT
<213> ORGANISM: Artificial sequence
<220> FEATURE:
<223> OTHER INFORMATION: generated by phage display

<400> SEQUENCE: 113

Tyr Gln Gly Tyr His Arg Ser Met Pro His Gly Ser
1               5                   10

<210> SEQ ID NO 114
<211> LENGTH: 12
<212> TYPE: PRT
<213> ORGANISM: Artificial sequence
<220> FEATURE:
<223> OTHER INFORMATION: generated by phage display

<400> SEQUENCE: 114

Ala Pro Leu Thr Ile Thr Arg Pro Leu Trp Pro Gly
1               5                   10

<210> SEQ ID NO 115
<211> LENGTH: 12
<212> TYPE: PRT
<213> ORGANISM: Artificial sequence
<220> FEATURE:
<223> OTHER INFORMATION: generated by phage display

<400> SEQUENCE: 115

Ala Pro Pro Met Ser Arg Gln Ser Phe Asp Gly Val
1               5                   10

<210> SEQ ID NO 116
<211> LENGTH: 12
<212> TYPE: PRT
<213> ORGANISM: Artificial sequence
<220> FEATURE:
<223> OTHER INFORMATION: generated by phage display

<400> SEQUENCE: 116

Ala Arg Phe Ile Gly Val Leu Trp Pro Pro Thr Asn
1               5                   10

<210> SEQ ID NO 117
<211> LENGTH: 12
<212> TYPE: PRT
<213> ORGANISM: Artificial sequence
```

```
<220> FEATURE:
<223> OTHER INFORMATION: generated by phage display

<400> SEQUENCE: 117

Asp Pro Ala Leu Arg His Thr His His Asn Leu Arg
1               5                   10

<210> SEQ ID NO 118
<211> LENGTH: 12
<212> TYPE: PRT
<213> ORGANISM: Artificial sequence
<220> FEATURE:
<223> OTHER INFORMATION: generated by phage display

<400> SEQUENCE: 118

Asp Val Ala Ile Ala Pro Lys Lys Ser Trp Val Val
1               5                   10

<210> SEQ ID NO 119
<211> LENGTH: 12
<212> TYPE: PRT
<213> ORGANISM: Artificial sequence
<220> FEATURE:
<223> OTHER INFORMATION: generated by phage display

<400> SEQUENCE: 119

Glu Glu Ala Asn Leu Ser Asn Val Pro Ser Trp Gly
1               5                   10

<210> SEQ ID NO 120
<211> LENGTH: 12
<212> TYPE: PRT
<213> ORGANISM: Artificial sequence
<220> FEATURE:
<223> OTHER INFORMATION: generated by phage display

<400> SEQUENCE: 120

Glu Gln His Pro Arg Phe Ser Gln His Leu Leu Leu
1               5                   10

<210> SEQ ID NO 121
<211> LENGTH: 12
<212> TYPE: PRT
<213> ORGANISM: Artificial sequence
<220> FEATURE:
<223> OTHER INFORMATION: generated by phage display

<400> SEQUENCE: 121

Phe Asn Leu Pro Ser Lys Asn Ser Ser Ile Ala Tyr
1               5                   10

<210> SEQ ID NO 122

<400> SEQUENCE: 122

000

<210> SEQ ID NO 123
<211> LENGTH: 12
<212> TYPE: PRT
<213> ORGANISM: Artificial sequence
<220> FEATURE:
<223> OTHER INFORMATION: generated by phage display

<400> SEQUENCE: 123

His Phe Trp Arg Pro Pro Thr Val Trp Ile Trp Pro
1               5                   10
```

<210> SEQ ID NO 124

<400> SEQUENCE: 124

000

<210> SEQ ID NO 125
<211> LENGTH: 12
<212> TYPE: PRT
<213> ORGANISM: Artificial sequence
<220> FEATURE:
<223> OTHER INFORMATION: generated by phage display

<400> SEQUENCE: 125

His Arg Trp Tyr Arg Trp Ser Ser Ser Asn Gln Thr
1               5                   10

<210> SEQ ID NO 126
<211> LENGTH: 12
<212> TYPE: PRT
<213> ORGANISM: Artificial sequence
<220> FEATURE:
<223> OTHER INFORMATION: generated by phage display

<400> SEQUENCE: 126

His Ser Ser Trp Trp Leu Ala Leu Asp Lys Pro Thr
1               5                   10

<210> SEQ ID NO 127
<211> LENGTH: 12
<212> TYPE: PRT
<213> ORGANISM: Artificial sequence
<220> FEATURE:
<223> OTHER INFORMATION: generated by phage display

<400> SEQUENCE: 127

His Trp Leu Pro His Asn Trp Glu Pro Val Ala Thr
1               5                   10

<210> SEQ ID NO 128
<211> LENGTH: 12
<212> TYPE: PRT
<213> ORGANISM: Artificial sequence
<220> FEATURE:
<223> OTHER INFORMATION: generated by phage display

<400> SEQUENCE: 128

His Trp Ser Ala Trp Trp Ile Leu Ser Asn Gln Ser
1               5                   10

<210> SEQ ID NO 129
<211> LENGTH: 12
<212> TYPE: PRT
<213> ORGANISM: Artificial sequence
<220> FEATURE:
<223> OTHER INFORMATION: generated by phage display

<400> SEQUENCE: 129

His Trp Trp Ala Trp Trp Ile Ser Ser Asn Gln Ser
1               5                   10

<210> SEQ ID NO 130
<211> LENGTH: 12
<212> TYPE: PRT
<213> ORGANISM: Artificial sequence
<220> FEATURE:
<223> OTHER INFORMATION: generated by phage display

```
<400> SEQUENCE: 130

Ile Tyr Lys Pro Gln Leu Lys Met Arg Leu Arg Leu
1               5                   10

<210> SEQ ID NO 131
<211> LENGTH: 12
<212> TYPE: PRT
<213> ORGANISM: Artificial sequence
<220> FEATURE:
<223> OTHER INFORMATION: generated by phage display

<400> SEQUENCE: 131

Lys Pro Pro Gln Met Pro Leu Tyr Asn Leu Ser Ala
1               5                   10

<210> SEQ ID NO 132
<211> LENGTH: 12
<212> TYPE: PRT
<213> ORGANISM: Artificial sequence
<220> FEATURE:
<223> OTHER INFORMATION: generated by phage display

<400> SEQUENCE: 132

Leu Val Leu Arg Ile Ser Gln Gly Gly Val Gly Pro
1               5                   10

<210> SEQ ID NO 133
<211> LENGTH: 12
<212> TYPE: PRT
<213> ORGANISM: Artificial sequence
<220> FEATURE:
<223> OTHER INFORMATION: generated by phage display

<400> SEQUENCE: 133

Met Pro His His Ala Leu Leu Gln Phe Pro Pro Pro
1               5                   10

<210> SEQ ID NO 134
<211> LENGTH: 12
<212> TYPE: PRT
<213> ORGANISM: Artificial sequence
<220> FEATURE:
<223> OTHER INFORMATION: generated by phage display

<400> SEQUENCE: 134

Asn Leu Asn Ser Thr Asn Pro Asn Leu Ile Pro Phe
1               5                   10

<210> SEQ ID NO 135
<211> LENGTH: 12
<212> TYPE: PRT
<213> ORGANISM: Artificial sequence
<220> FEATURE:
<223> OTHER INFORMATION: generated by phage display

<400> SEQUENCE: 135

Gln Glu Ile Leu Ser Pro Pro Ser Pro Leu His Ser
1               5                   10

<210> SEQ ID NO 136
<211> LENGTH: 12
<212> TYPE: PRT
<213> ORGANISM: Artificial sequence
<220> FEATURE:
<223> OTHER INFORMATION: generated by phage display

<400> SEQUENCE: 136
```

```
Gln Asn Ser Ser Met Met Leu Val Pro Trp Arg Thr
1               5                   10
```

<210> SEQ ID NO 137
<211> LENGTH: 12
<212> TYPE: PRT
<213> ORGANISM: Artificial sequence
<220> FEATURE:
<223> OTHER INFORMATION: generated by phage display

<400> SEQUENCE: 137

```
Ser Ile Ile Thr Thr Pro Ala Ser Tyr Met Asp Tyr
1               5                   10
```

<210> SEQ ID NO 138
<211> LENGTH: 12
<212> TYPE: PRT
<213> ORGANISM: Artificial sequence
<220> FEATURE:
<223> OTHER INFORMATION: generated by phage display

<400> SEQUENCE: 138

```
Ser Leu Ser Asn Phe Lys Asn Pro Thr Gln Ala Pro
1               5                   10
```

<210> SEQ ID NO 139
<211> LENGTH: 12
<212> TYPE: PRT
<213> ORGANISM: Artificial sequence
<220> FEATURE:
<223> OTHER INFORMATION: generated by phage display

<400> SEQUENCE: 139

```
Ser Asn Ile His Ser Arg Tyr Pro Leu Trp Leu Arg
1               5                   10
```

<210> SEQ ID NO 140
<211> LENGTH: 12
<212> TYPE: PRT
<213> ORGANISM: Artificial sequence
<220> FEATURE:
<223> OTHER INFORMATION: generated by phage display

<400> SEQUENCE: 140

```
Ser Pro Ser Pro His Ser His Asp His Leu Phe Lys
1               5                   10
```

<210> SEQ ID NO 141
<211> LENGTH: 12
<212> TYPE: PRT
<213> ORGANISM: Artificial sequence
<220> FEATURE:
<223> OTHER INFORMATION: generated by phage display

<400> SEQUENCE: 141

```
Ser Val Pro Val Thr Lys Asn Pro Leu Pro Pro Arg
1               5                   10
```

<210> SEQ ID NO 142
<211> LENGTH: 12
<212> TYPE: PRT
<213> ORGANISM: Artificial sequence
<220> FEATURE:
<223> OTHER INFORMATION: generated by phage display

<400> SEQUENCE: 142

```
Ser Val Ser Val Gly Met Lys Pro Ser His Arg Pro
1               5                   10
```

-continued

<210> SEQ ID NO 143
<211> LENGTH: 12
<212> TYPE: PRT
<213> ORGANISM: Artificial sequence
<220> FEATURE:
<223> OTHER INFORMATION: generated by phage display

<400> SEQUENCE: 143

Ser Tyr Trp Pro Pro Ala Pro Pro Leu Asn Thr Phe
1               5                   10

<210> SEQ ID NO 144
<211> LENGTH: 12
<212> TYPE: PRT
<213> ORGANISM: Artificial sequence
<220> FEATURE:
<223> OTHER INFORMATION: generated by phage display

<400> SEQUENCE: 144

Thr Phe Asn Pro Ala Val Asn Ala Ser Ser Leu Ser
1               5                   10

<210> SEQ ID NO 145
<211> LENGTH: 12
<212> TYPE: PRT
<213> ORGANISM: Artificial sequence
<220> FEATURE:
<223> OTHER INFORMATION: generated by phage display

<400> SEQUENCE: 145

Thr Pro Trp Phe Gln Trp His Gln Trp Asn Leu Asn
1               5                   10

<210> SEQ ID NO 146
<211> LENGTH: 12
<212> TYPE: PRT
<213> ORGANISM: Artificial sequence
<220> FEATURE:
<223> OTHER INFORMATION: generated by phage display

<400> SEQUENCE: 146

Val Asn Gln Lys Asn Ile Pro His Ala Thr His Phe
1               5                   10

<210> SEQ ID NO 147
<211> LENGTH: 12
<212> TYPE: PRT
<213> ORGANISM: Artificial sequence
<220> FEATURE:
<223> OTHER INFORMATION: generated by phage display

<400> SEQUENCE: 147

Tyr Gln Gly His Ala Pro Trp Pro Ile Ile Pro His
1               5                   10

<210> SEQ ID NO 148
<211> LENGTH: 12
<212> TYPE: PRT
<213> ORGANISM: Artificial sequence
<220> FEATURE:
<223> OTHER INFORMATION: generated by phage display

<400> SEQUENCE: 148

Ala Leu Thr Pro Phe Tyr Gln Ala Ile Gly Ser Arg
1               5                   10

```
<210> SEQ ID NO 149
<211> LENGTH: 12
<212> TYPE: PRT
<213> ORGANISM: Artificial sequence
<220> FEATURE:
<223> OTHER INFORMATION: generated by phage display

<400> SEQUENCE: 149

Ala Ser Ser Val Pro Leu Ser Val Arg Leu Ala His
1               5                   10

<210> SEQ ID NO 150
<211> LENGTH: 12
<212> TYPE: PRT
<213> ORGANISM: Artificial sequence
<220> FEATURE:
<223> OTHER INFORMATION: generated by phage display

<400> SEQUENCE: 150

Asp Phe Thr Met Gly Gln His Pro Ser Lys His Thr
1               5                   10

<210> SEQ ID NO 151
<211> LENGTH: 12
<212> TYPE: PRT
<213> ORGANISM: Artificial sequence
<220> FEATURE:
<223> OTHER INFORMATION: generated by phage display

<400> SEQUENCE: 151

Asp Ser Phe Pro Thr Pro Met Arg Ala Leu Ala Ala
1               5                   10

<210> SEQ ID NO 152
<211> LENGTH: 12
<212> TYPE: PRT
<213> ORGANISM: Artificial sequence
<220> FEATURE:
<223> OTHER INFORMATION: generated by phage display

<400> SEQUENCE: 152

Asp Thr Arg Gln Ala Thr His Gly Ala Tyr Arg Leu
1               5                   10

<210> SEQ ID NO 153
<211> LENGTH: 12
<212> TYPE: PRT
<213> ORGANISM: Artificial sequence
<220> FEATURE:
<223> OTHER INFORMATION: generated by phage display

<400> SEQUENCE: 153

Glu Thr Val Phe Phe His Thr Met Gln Ser Pro Glu
1               5                   10

<210> SEQ ID NO 154
<211> LENGTH: 12
<212> TYPE: PRT
<213> ORGANISM: Artificial sequence
<220> FEATURE:
<223> OTHER INFORMATION: generated by phage display

<400> SEQUENCE: 154

Phe Ser Leu Gln Ser His Tyr Pro Phe Pro Ser Leu
1               5                   10

<210> SEQ ID NO 155
<211> LENGTH: 12
```

```
<212> TYPE: PRT
<213> ORGANISM: Artificial sequence
<220> FEATURE:
<223> OTHER INFORMATION: generated by phage display

<400> SEQUENCE: 155

Gly Pro Met Ser Glu Arg Ala Pro Ser Phe Thr Ile
1               5                   10

<210> SEQ ID NO 156
<211> LENGTH: 12
<212> TYPE: PRT
<213> ORGANISM: Artificial sequence
<220> FEATURE:
<223> OTHER INFORMATION: generated by phage display

<400> SEQUENCE: 156

His Gly Trp His Tyr Tyr Leu Arg Thr Gln His Ser
1               5                   10

<210> SEQ ID NO 157
<211> LENGTH: 12
<212> TYPE: PRT
<213> ORGANISM: Artificial sequence
<220> FEATURE:
<223> OTHER INFORMATION: generated by phage display

<400> SEQUENCE: 157

His His His His Leu Arg His Pro Phe Trp Thr His
1               5                   10

<210> SEQ ID NO 158
<211> LENGTH: 12
<212> TYPE: PRT
<213> ORGANISM: Artificial sequence
<220> FEATURE:
<223> OTHER INFORMATION: generated by phage display

<400> SEQUENCE: 158

His Lys Trp Pro Leu Thr Lys Leu Pro Glu Phe Pro
1               5                   10

<210> SEQ ID NO 159
<211> LENGTH: 12
<212> TYPE: PRT
<213> ORGANISM: Artificial sequence
<220> FEATURE:
<223> OTHER INFORMATION: generated by phage display

<400> SEQUENCE: 159

His Leu Thr Asp Ser Thr Leu Arg Gly Leu Leu Pro
1               5                   10

<210> SEQ ID NO 160
<211> LENGTH: 12
<212> TYPE: PRT
<213> ORGANISM: Artificial sequence
<220> FEATURE:
<223> OTHER INFORMATION: generated by phage display

<400> SEQUENCE: 160

His Met Tyr His His Asn Ile Leu Glu Arg His Pro
1               5                   10

<210> SEQ ID NO 161
<211> LENGTH: 12
<212> TYPE: PRT
<213> ORGANISM: Artificial sequence
```

```
<220> FEATURE:
<223> OTHER INFORMATION: generated by phage display
<220> FEATURE:
<221> NAME/KEY: MISC_FEATURE
<222> LOCATION: (10)..(10)
<223> OTHER INFORMATION: Xaa can be any amino acid

<400> SEQUENCE: 161

His Asn Pro His Thr Val Trp Thr Thr Xaa Ala His
1               5                   10

<210> SEQ ID NO 162
<211> LENGTH: 12
<212> TYPE: PRT
<213> ORGANISM: Artificial sequence
<220> FEATURE:
<223> OTHER INFORMATION: generated by phage display

<400> SEQUENCE: 162

His Pro His Leu Phe Thr Lys Leu Leu Thr Tyr Lys
1               5                   10

<210> SEQ ID NO 163
<211> LENGTH: 12
<212> TYPE: PRT
<213> ORGANISM: Artificial sequence
<220> FEATURE:
<223> OTHER INFORMATION: generated by phage display

<400> SEQUENCE: 163

His Gln Gln Ser Tyr His Gly Ser Arg Trp Thr Pro
1               5                   10

<210> SEQ ID NO 164
<211> LENGTH: 12
<212> TYPE: PRT
<213> ORGANISM: Artificial sequence
<220> FEATURE:
<223> OTHER INFORMATION: generated by phage display

<400> SEQUENCE: 164

Lys Ala Pro Val Ser Phe Ser Ile His Pro Ala Trp
1               5                   10

<210> SEQ ID NO 165
<211> LENGTH: 12
<212> TYPE: PRT
<213> ORGANISM: Artificial sequence
<220> FEATURE:
<223> OTHER INFORMATION: generated by phage display

<400> SEQUENCE: 165

Lys Thr Cys Asn Thr Thr Arg Pro Cys Trp Asn Pro
1               5                   10

<210> SEQ ID NO 166
<211> LENGTH: 12
<212> TYPE: PRT
<213> ORGANISM: Artificial sequence
<220> FEATURE:
<223> OTHER INFORMATION: generated by phage display

<400> SEQUENCE: 166

Leu Asp Lys His His Leu Arg Met Tyr Ser Leu Lys
1               5                   10

<210> SEQ ID NO 167
<211> LENGTH: 12
```

```
<212> TYPE: PRT
<213> ORGANISM: Artificial sequence
<220> FEATURE:
<223> OTHER INFORMATION: generated by phage display

<400> SEQUENCE: 167

Asn Met Thr Gly Ala Leu Phe Thr Pro His Ser Phe
1               5                   10

<210> SEQ ID NO 168
<211> LENGTH: 12
<212> TYPE: PRT
<213> ORGANISM: Artificial sequence
<220> FEATURE:
<223> OTHER INFORMATION: generated by phage display

<400> SEQUENCE: 168

Gln Ala Asp Leu Lys Thr Pro Pro His Gln Arg Leu
1               5                   10

<210> SEQ ID NO 169
<211> LENGTH: 12
<212> TYPE: PRT
<213> ORGANISM: Artificial sequence
<220> FEATURE:
<223> OTHER INFORMATION: generated by phage display

<400> SEQUENCE: 169

Ser Asn Gly Pro Gln His Ser His Val Thr Ser Ser
1               5                   10

<210> SEQ ID NO 170
<211> LENGTH: 12
<212> TYPE: PRT
<213> ORGANISM: Artificial sequence
<220> FEATURE:
<223> OTHER INFORMATION: generated by phage display

<400> SEQUENCE: 170

Ser Ser Tyr His His Pro Asn Phe Leu Val Ala Ala
1               5                   10

<210> SEQ ID NO 171
<211> LENGTH: 12
<212> TYPE: PRT
<213> ORGANISM: Artificial sequence
<220> FEATURE:
<223> OTHER INFORMATION: generated by phage display

<400> SEQUENCE: 171

Thr Leu Lys Val Ser Thr Leu Thr Met Gly Ala Arg
1               5                   10

<210> SEQ ID NO 172
<211> LENGTH: 12
<212> TYPE: PRT
<213> ORGANISM: Artificial sequence
<220> FEATURE:
<223> OTHER INFORMATION: generated by phage display

<400> SEQUENCE: 172

Thr Ser Ile Ser Tyr Ser Glu Leu Thr Pro His Thr
1               5                   10

<210> SEQ ID NO 173
<211> LENGTH: 12
<212> TYPE: PRT
<213> ORGANISM: Artificial sequence
```

```
<220> FEATURE:
<223> OTHER INFORMATION: generated by phage display

<400> SEQUENCE: 173

Val Glu Asp Asn Pro Pro Ala Leu Leu Val Ser Pro
1               5                   10

<210> SEQ ID NO 174
<211> LENGTH: 12
<212> TYPE: PRT
<213> ORGANISM: Artificial sequence
<220> FEATURE:
<223> OTHER INFORMATION: generated by phage display

<400> SEQUENCE: 174

Val Val Asn Lys Thr Leu Lys Pro Thr Pro Val Ser
1               5                   10

<210> SEQ ID NO 175
<211> LENGTH: 12
<212> TYPE: PRT
<213> ORGANISM: Artificial sequence
<220> FEATURE:
<223> OTHER INFORMATION: generated by phage display

<400> SEQUENCE: 175

Trp Pro His His Pro His Ala Ala His Thr Ile Arg
1               5                   10

<210> SEQ ID NO 176
<211> LENGTH: 12
<212> TYPE: PRT
<213> ORGANISM: Artificial sequence
<220> FEATURE:
<223> OTHER INFORMATION: generated by phage display

<400> SEQUENCE: 176

Tyr Val Ala Met Pro Pro Ile Tyr Pro Asn Pro Gly
1               5                   10

<210> SEQ ID NO 177
<211> LENGTH: 12
<212> TYPE: PRT
<213> ORGANISM: Artificial sequence
<220> FEATURE:
<223> OTHER INFORMATION: generated by phage display

<400> SEQUENCE: 177

His Asn Trp Tyr His Trp Trp Met Pro His Lys Thr
1               5                   10
```